US007517397B2

(12) United States Patent
Campbell et al.

(10) Patent No.: US 7,517,397 B2
(45) Date of Patent: Apr. 14, 2009

(54) HEAT SENSITIVE RECORDING MATERIAL

(75) Inventors: Jonathan Campbell, Oldham (GB); Robert Montgomery O'Neil, Manchester (GB); Ian Street, Manchester (GB); William Walker, Manchester (GB); John Whitworth, Manchester (GB)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 485 days.

(21) Appl. No.: 10/553,778

(22) PCT Filed: Apr. 26, 2004

(86) PCT No.: PCT/EP2004/050607

§ 371 (c)(1),
(2), (4) Date: Oct. 20, 2005

(87) PCT Pub. No.: WO2004/099116

PCT Pub. Date: Nov. 18, 2004

(65) Prior Publication Data

US 2006/0240981 A1  Oct. 26, 2006

(30) Foreign Application Priority Data

May 9, 2003  (GB) ................. 0310685.3

(51) Int. Cl.
*B41M 5/333* (2006.01)
*C09D 10/00* (2006.01)
(52) U.S. Cl. .................... 106/31.18; 503/216
(58) Field of Classification Search ................ None
See application file for complete search history.

(56) References Cited

U.S. PATENT DOCUMENTS

| 2,830,970 | A | 4/1958 | Tawney | 260/62 |
| 4,608,579 | A | 8/1986 | Taniguchi | 346/209 |
| 6,395,680 | B1 | 5/2002 | Morita et al. | 503/216 |

FOREIGN PATENT DOCUMENTS

| GB | 978853 | 12/1964 |
| JP | 60-259494 | 12/1985 |
| JP | 1995118209 | 5/1995 |
| JP | 7-118209 | 7/1995 |
| JP | 7-173108 | 7/1995 |
| JP | 1995173108 | 7/1995 |
| JP | 2000-302732 | 10/2000 |

OTHER PUBLICATIONS

English Language abstract of JP 60-259494.
Patent abstracts of Japan vol. 2000, No. 13 (Feb. 2001) of JP 2000/302732.
Patent abstracts of Japan vol. 010, No. 292 (Oct. 1986) of JP 61 109757.
Patent abstract of Japan vol. 1995, No. 08, (Sep. 1995) of JP 07 118209.
Patent abstract of Japan vol. 1995, No. 10, (Nov. 1995) of JP 07 173108.
Bai et al. XP-002300422, AN 2000-36977, Oct. 2004.
Shin et al. XP-002300423, AN 1999:436044, Oct. 2004.
Rosenthal et al., Journal f. Prakt. Chemie. Band 328, Heft 3, 1986, S. pp. 335-341.
Haeberlein et al., Die Angewandte Makromolekulare Chemie, vol. 33, (1973) pp. 111-127 (Nr. 487).
Wenkert et al., Journal of Organic Chemistry, vol. 29, No. 9, (Sep. 1964), pp. 2534-2542.
Barton et al., Journal of the Chemical Society, Perkin Transactions 1: Organic and Bio-organic Chemistry vol. 7, 1974, pp. 781-792.
Sasaki et al., Angewandte Chemie, International edition, vol. 41, No. 16 2002, pp. 3005-3007.
Drechsler et al. J. Prakt. Chem. vol. 23, 1964, pp. 10-18.
Database AN BRN 3520032 abstract of—Niederl et al. Ind. Eng. Chem. vol. 30, 1938, pp. 1269-1272.
Alcalde et al., J. Org. Chem. 2001, vol. 66, pp. 2291-2295.
Database AN BRN 2684300 abstract of Starratt, Can. J. Chem. 46, 1968 pp. 767-770.
Database AN BRN 7606148 abstract of Molony et al, Tetrahedron Asymmetry, vol. 7, No. 9, 1996, pp. 2551-2562.
Database AN BRN 9299521 abstract of Iwamoto et al. Tetrahetron Let. vol. 43, No. 45, 2002 pp. 8191-8194.

*Primary Examiner*—Bruce H Hess
(74) *Attorney, Agent, or Firm*—Tyler A. Stevenson

(57) ABSTRACT

New color developers, new mixture comprising it, its processes for preparation, heat sensitive recording compositions and materials comprising the novel developers and mixtures as well as their uses in heat sensitive recording materials.

7 Claims, No Drawings

HEAT SENSITIVE RECORDING MATERIAL

The present invention relates to heat sensitive recording materials. It more particularly relates to such recording material in the form of a supporting substrate, for example, a paper sheet, synthetic paper sheet or plastic resin film coated with colour-forming systems comprising a colourless or pale coloured electron donative compound (colour forming compound) and an organic electron acceptor (colour developer).

Heat sensitive recording has conventionally been used as a system for recording transferred information through the mediation of heat, by utilising a colour reaction between a colour forming compound and a colour developer.

The properties which are most desirable in a heat sensitive recording material, in addition to the effective development of colour, are thermal response, background whiteness and image stability, especially light fastness of the developed colour, heat and moisture fastness of the developed colour, oil fastness of the developed colour, plasticiser resistance of the developed colour and water fastness of the developed colour.

JP-A 61-109757 claims developing compounds of the formula

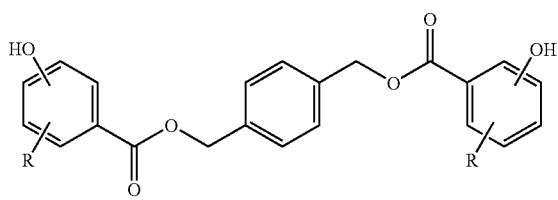

wherein R means hydrogen or hydroxy, as well as a thermosensitive recording material, characterized in containing colorless or pale color-developing dyestuffs, which develop color by means of electron accepting material and the abovementioned colour developing compound.

A need exists to improve the above properties and to improve the archival capabilities of such recording materials. It is an object of the present invention to provide heat sensitive recording materials with improved properties, especially to provide an increase in image stability whilst improving the background whiteness of the paper before imaging and the background whiteness of the undeveloped portion after imaging.

Therefore, the present invention is directed to a colour developer of the formula (1)

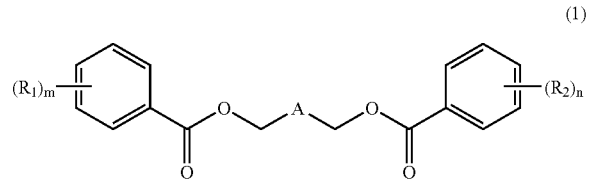

wherein

A stands for a unsubstituted or substituted divalent aromatic radical, preferably for phenylene, biphenylene, naphthylene, or anthrylene, more preferably for

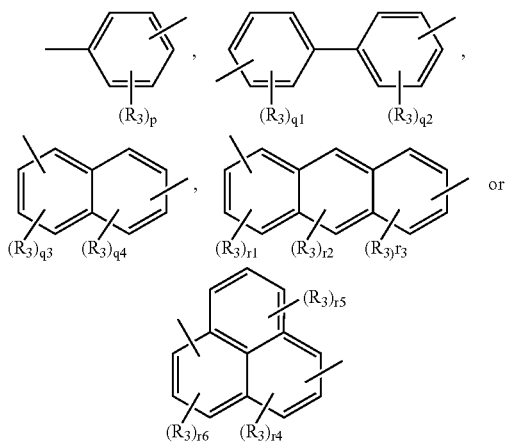

$R_1$ and $R_2$ are independent of each other and stand for —OH, unsubstituted or substituted $C_1$-$C_8$alkyl, unsubstituted or substituted $C_1$-$C_8$alkoxy, unsubstituted or substituted phenyl or naphthyl, —COOR$_{1a}$, wherein $R_{1a}$ stands for hydrogen, unsubstituted or substituted $C_1$-$C_8$alkyl, benzyl or unsubstituted or substituted phenyl, —C(O)R$_{1a}$, or —NR$_{1a}$R$_{1b}$, wherein $R_{1b}$, independently from $R_{1a}$, stands for hydrogen, unsubstituted or substituted $C_1$-$C_8$alkyl, benzyl or unsubstituted or substituted phenyl, $R_3$ stands for hydrogen, hydroxy, unsubstituted or substituted phenyl or naphthyl, unsubstituted or substituted $C_1$-$C_{24}$alkyl, unsubstituted or substituted $C_5$-$C_{10}$cycloalkyl, unsubstituted or substituted $C_1$-$C_{24}$alkoxy, unsubstituted or substituted phenyoxy or naphthyloxy, halomethyl, —COOR$_4$, wherein $R_4$ stands for hydrogen or $C_1$-$C_8$alkyl, —CONR$_5$R$_6$, wherein $R_5$ and $R_6$, independently from each other stand for hydrogen or $C_1$-$C_8$alkyl, or —NO$_2$, m stands for 0, 1, 2, 3, 4 or 5, n stands for 0, 1, 2, 3, 4, or 5, p, q1 and q2, independently from each other stand for 0, 1, 2, 3, 4, q3, q4, r1, r3 and r5, independently from each other, stand for 0, 1, 2, or 3, r2, r4 and r6, independently from each other, stand for 0, 1 or 2, with the proviso, that if A stands for para-phenylen, $R_1$ for hydroxy (m≠0), then $R_2$ is not hydroxy.

$R_1$, $R_2$, and $R_3$ as phenyl or naphthyl or $R_{1a}$ and $R_{1b}$ as phenyl can be unsubstituted or substituted, preferably one to three times, by, for example, $C_1$-$C_8$alkyl, $C_1$-$C_8$alkoxy or halogen. Preferred substituents are $C_1$-$C_4$alkyl, especially methyl or ethyl, $C_1$-$C_4$alkoxy, especially methoxy or ethoxy, or halogen, especially chlorine. $R_1$, $R_2$ and $R_3$ as naphthyl are preferably unsubstituted. $R_1$ and $R_2$ as phenyl are preferably substituted, especially by one of the above alkyl substituents, $R_3$, $R_{1a}$, and $R_{1b}$ as phenyl preferably are unsubstituted.

$R_1$, $R_2$, $R_{1a}$ and $R_{1b}$ as $C_1$-$C_8$alkyl can be unsubstituted or substituted, one to three times, by, for example $C_1$-$C_8$alkoxy or halogen. Preferred substituents are $C_1$-$C_4$alkoxy, especially methoxy or ethoxy, or halogen, especially chlorine. $R_1$, $R_2$, $R_{1a}$ and $R_{1b}$ as $C_1$-$C_8$alkyl are preferably unsubstituted.

$R_3$ as $C_1$-$C_{24}$alkyl can be unsubstituted or substituted, one to three times, by, for example $C_1$-$C_8$alkoxy or halogen. Preferred substituents are $C_1$-$C_4$alkoxy, especially methoxy or ethoxy, or halogen, especially chlorine.

Preferably, at least one of $R_1$ or $R_2$ is hydroxy.

Another embodiment of the present invention relates to a mature consisting of (a) a color developer (1a)

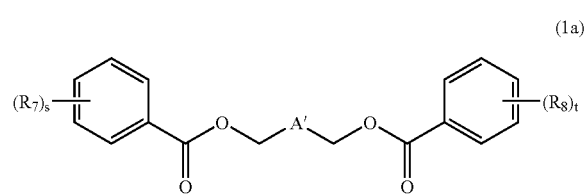

wherein

A' stands for a unsubstituted or substituted divalent aromatic radical, preferably for phenylene, biphenylene, naphthylene, or anthrylene, more preferably for

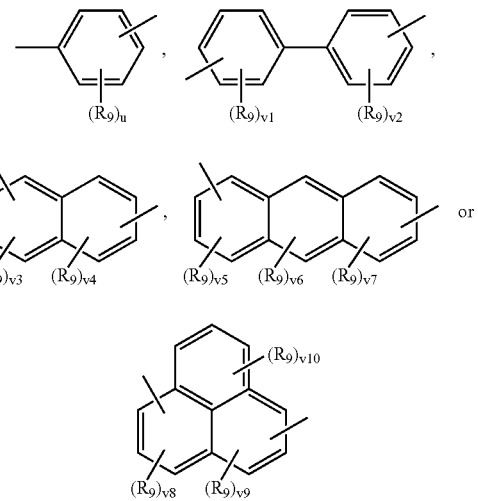

$R_7$ and $R_8$ are independent of each other and stand for —OH, unsubstituted or substituted $C_1$-$C_8$alkyl, unsubstituted or substituted $C_1$-$C_8$alkoxy, unsubstituted or substituted phenyl or naphthyl, —COOR$_{1a}$, wherein $R_{1a}$ stands for hydrogen, unsubstituted or substituted $C_1$-$C_8$alkyl, benzyl or unsubstituted or substituted phenyl, —C(O)R$_{1a}$, or —NR$_{1a}$R$_{1b}$, wherein R$_{1b}$, independently from R$_{1a}$, stands for hydrogen, unsubstituted or substituted $C_1$-$C_8$alkyl, benzyl or unsubstituted or substituted phenyl, $R_9$ stands for hydrogen, hydroxy, unsubstituted or substituted phenyl or naphthyl, unsubstituted or substituted $C_1$-$C_{24}$alkyl, unsubstituted or substituted $C_5$-$C_{10}$cycloalkyl, unsubstituted or substituted $C_1$-$C_{24}$alkoxy, unsubstituted or substituted phenyoxy or naphthyloxy, halomethyl, —COOR$_{10}$, wherein R$_{10}$ stands for hydrogen or $C_1$-$C_8$alkyl, —CONR$_{11}$R$_{12}$, wherein R$_{11}$ and R$_{12}$, independently from each other stand for hydrogen or $C_1$-$C_8$alkyl, or —NO$_2$, s stands for 0, 1, 2, 3, 4 or 5, t stands for 0, 1, 2, 3, 4, or 5, u stands for 0, 1, 2, 3, 4, v1 and v2, independently from each other, stand for 0, 1, 2, 3, or 4, v3, v4, v5, v7, and v10, independently from each other, stand for 0, 1, 2, or 3, v6, v8 and v9, independently from each other stand for 0, 1 or 2, and (b) a compound of formula (2)

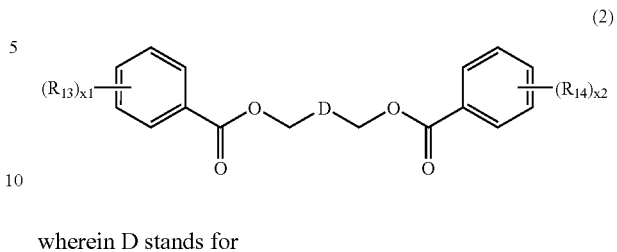

wherein D stands for

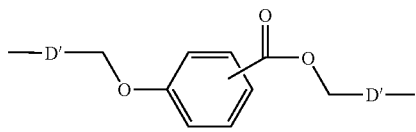

wherein D' stands for a unsubstituted or substituted divalent aromatic radical, preferably for phenylene, biphenylene, naphthylene, or anthrylene, more preferably for

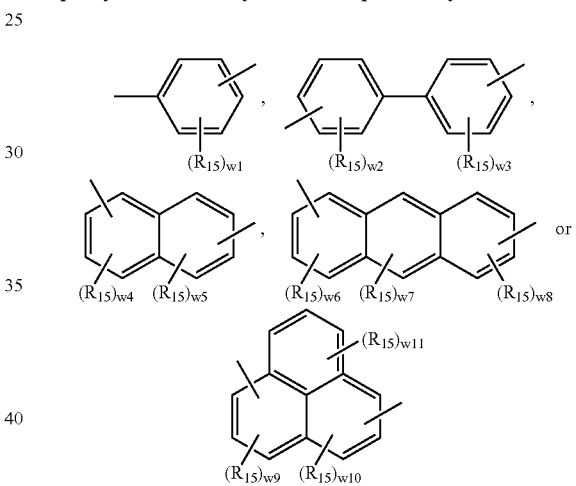

wherein $R_{13}$ stands for a substituent as defined for $R_7$, $R_{14}$ stands for a substituent as defined for $R_8$, $R_{15}$ stands for a substituent as defined for $R_9$, w1 stands for 0, 1, 2, 3, 4 or 5, w2 and w3, independently from each other, stand for 0, 1, 2, 3, or 4, w4, w5, w6, w8 and w11, independently from each other, stand for 0, 1, 2, or 3, w7, w9 and w10, independently from each other stand for 0, 1 or 2, and wherein the weight ratio of (1a) to (2) is chosen in the range from 99.9:0.1 to 0.1:99.9, preferably from 95:5 to 70:30.

$R_7$, $R_8$, and $R_9$ as phenyl or naphthyl can be unsubstituted or substituted, preferably one to three times, by, for example, $C_1$-$C_8$alkyl, $C_1$-$C_8$alkoxy or halogen. Preferred substituents are $C_1$-$C_4$alkyl, especially methyl or ethyl, $C_1$-$C_4$alkoxy, especially methoxy or ethoxy, or halogen, especially chlorine. $R_7$, $R_8$ and $R_9$ as naphthyl are preferably unsubstituted. $R_7$ and $R_8$ as phenyl are preferably substituted, especially by one of the above alkyl substituents, $R_9$ as phenyl preferably is unsubstituted.

$R_7$ and $R_8$ as $C_1$-$C_8$alkyl can be unsubstituted or substituted, preferably one to three times, by, for example $C_1$-$C_8$alkoxy or halogen. Preferred substituents are $C_1$-$C_4$alkoxy, especially methoxy or ethoxy, or halogen, especially chlorine. $R_7$ and $R_8$ as $C_1$-$C_8$alkyl are preferably unsubstituted.

$R_9$ as $C_1$-$C_{24}$alkyl can be unsubstituted or substituted, preferably one to three times, by, for example $C_1$-$C_8$alkoxy or halogen. Preferred substituents are $C_1$-$C_4$alkoxy, especially methoxy or ethoxy, or halogen, especially chlorine.

$C_1$-$C_{24}$alkyl e.g. stands for methyl, ethyl, n-propyl, i-propyl, n-, i-, sec., tert. butyl, n-, i-, tert.-pentyl, n-hexyl, n-heptyl, n-octyl, 2-ethyl-hexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-uneicosyl, n-doeicosyl, n-trieicosyl, n-tetraeicosyl, preferably for $C_1$-$C_8$alkyl such as defined below.

$C_1$-$C_8$alkyl e.g. stands for methyl, ethyl, n-propyl, i-propyl, n-, i-, sec., tert butyl, n-, i-, tert-pentyl, n-hexyl, n-heptyl, n-octyl, 2-ethylhexyl, preferably for $C_1$-$C_6$alkyl such as methyl, ethyl, n-propyl, i-propyl, n-, i-, sec., tert. butyl, n-, i-, tert.-pentyl, n-hexyl, particular preferred for $C_1$-$C_4$alkyl such as methyl, ethyl, n-propyl, i-propyl, n-, i-, sec., tert. butyl.

$C_1$-$C_{24}$alkoxy e.g. stands for methoxy, ethoxy, n-propoxy, n-butoxy, n-pentoxy, n-hexoxy, n-heptoxy, n-octoxy, 2-ethylhexoxy, n-nonoxy, n-decoxy, n-undecoxy, n-dodecoxy, n-tridecoxy, n-tetradecoxy, n-pentadecoxy, n-hexadecoxy, n-heptadecoxy, n-octadecoxy, n-nonadecoxy, n-eicosoxy, n-uneicosoxy, n-doeicosoxy, n-trieicosoxy, n-tetraeicosoxy, preferably for $C_1$-$C_8$alkoxy such as defined below.

$C_1$-$C_8$alkoxy e.g. stands for methoxy, ethoxy, n-, i-propoxy, n-butoxy, n-pentoxy, n-hexoxy, n-heptoxy, n-octoxy, preferably for $C_1$-$C_4$alkoxy such as methoxy, ethoxy, n-, i-propoxy, n-butoxy.

$C_5$-$C_{10}$cycloalkyl stands for e.g. cyclopentyl, cyclohexyl, cycloheptyl, cyclooctyl, cyclononyl, cyclodecyl, preferably cyclopentyl and cycylohexyl.

A further embodiment of this invention relates to compounds of formula (2) as well as their use as colour developers.

A particularly preferred compound (1) or (1a) is represented by formula (1b)

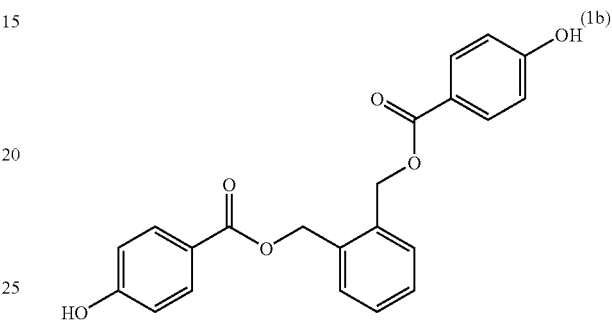

A particularly preferred mixture is a mixture of the following two compounds (1b) and (2a)

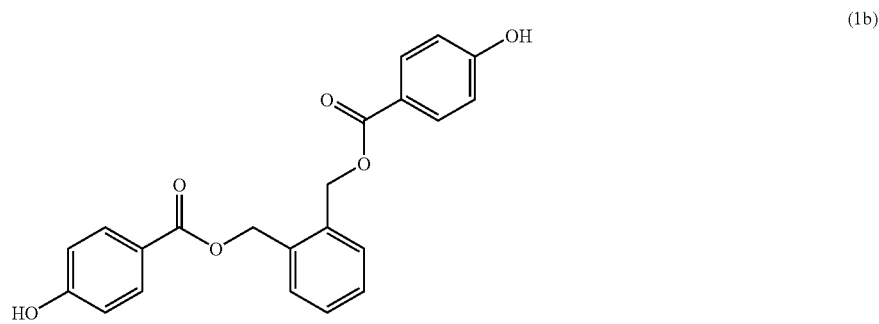

(1b)

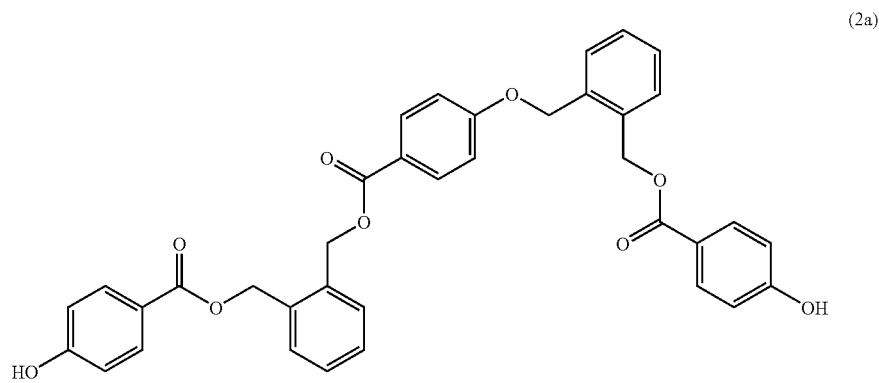

(2a)

wherein the weight ratio of (1b) and (2a) is chosen in the range of 99.9:0.1 to 0.1:99.9, preferably from 95:5 to 70:30.

The compounds of formula (1) resp. (1a) can be prepared e.g. via the following route, in particular, should $R_{16}$ be different from $R_{17}$:

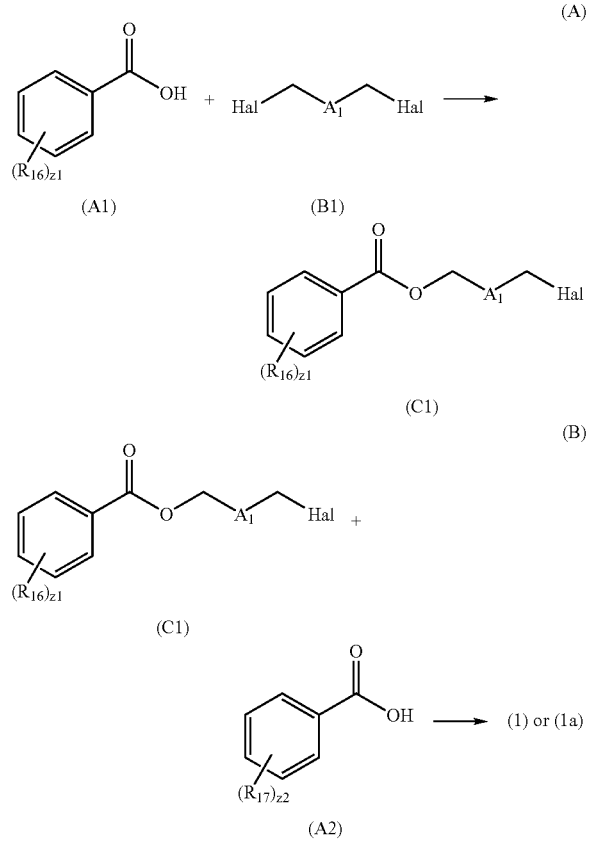

wherein $R_{16}$ stands for a substituent as defined for $R_7$, and $A_1$ for A or A', $R_{17}$ stands for a substituent as defined for $R_8$, z1 for an integer a defined for s, and z2 for an integer as defined for t, and wherein Hal stands for halogen, preferably for chloro or bromo. Ester derivatives of formula (1) or (1a) may also be synthesized from a suitable dihydroxy compound, for example 1,2-benzenedimethanol.

Usually the benzoic acid derivative (A1) is reacted with a dihalogen derivative (B1) in a solvent at a temperature in the range of from 0 to 100° C. The duration of the reaction usually depends on inter alia the temperature and the reactivity of the educts, but as a rule the duration is chosen in the range of from 5 minutes to 48 hours. As solvent the following solvents or their mixtures can be used: N,N-dimethyl-acetamide, N,N-dimethylformamide, dimethyl sulfoxide, acetone, tetrahydrofuran, 1,4-dioxane, acetonitrile, sulfolane, hexamethylphosphoramide, polyethylene glycols ("PEG"), alcohols such as methanol, ethanol, n-, i-propanol, n-butanol, alkyl amines such as triethylamine, tripropylamine, triethanolamine or water. Of course, the above list is not completed, but exhibits the variety of different solvents, which can be used. The reaction may also be carried out in the absence of a solvent.

In a preferred embodiment a base is added to the reaction mixture in order to neutralize the liberated acid. A number of different bases can be chosen including both organic and inorganic bases. Suitable bases are exemplified, but not limited to the following: alkali metal carbonates, alkali metal bicarbonates such as potassium bicarbonate, alkaline earth metal oxides, amines, pyridines, alkali metal hydroxides such as sodium hydroxide or potassium hydroxide or the corresponding ammonium hydroxides such as such as tetrabutyl ammonium hydroxide.

The molar ratio of (A1) to (B1) usually depends on whether $R_{16}$ is the same as $R_{17}$ or different. If $R_{16}$ is the same as $R_{17}$ then the molar ratio is chosen in the range of from 3:1 to 10:1. If $R_{16}$ and $R_{17}$ are different then the total amount of (A1)+ (A2), based on the amount of (B1), preferably is chosen in the range of from 3:1 to 10:1, wherein the amounts of (A1) and (A2) preferably are the same.

Generally, the weight ratio of solvent to compound (A1) is chosen in the range of from 20:1 to 0:1, preferably from 20:1 to 0.1:1.

After reaction, the reaction products can be isolated by methods known in the art. These are exemplified by, but not limited to, distillation, crystallisation, precipitation, addition of a non-solvent, extraction, filtration, centrifugation etc.

Therefore, another embodiment of the present invention relates to a process for the manufacture of a colour developer of formula (1) by reacting a benzoic acid derivative with a dihalogen derivative, in which (a) benzoic acid derivative of formula (A1)

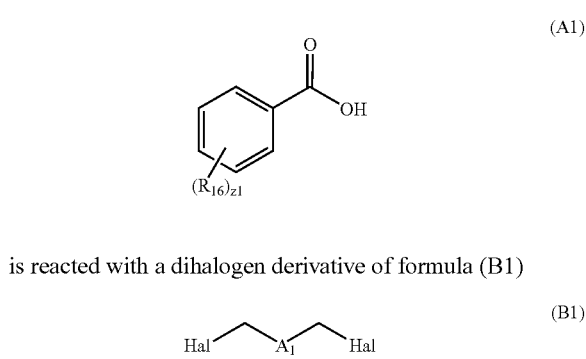

is reacted with a dihalogen derivative of formula (B1)

(B1)

$$Hal\diagup A_1\diagdown Hal$$

wherein $R_{16}$ stands for —OH, unsubstituted or substituted $C_1$-$C_8$alkyl, unsubstituted or substituted $C_1$-$C_8$alkoxy, unsubstituted or substituted phenyl or naphthyl, —COOR$_{1a}$, wherein $R_{1a}$ stands for hydrogen, unsubstituted or substituted $C_1$-$C_8$alkyl, benzyl or unsubstituted or substituted phenyl, —C(O)R$_{1a}$, or —NR$_{1a}$R$_{1b}$, wherein R$_{1b}$, independently from R$_{1a}$, stands for hydrogen, unsubstituted or substituted $C_1$-$C_8$alkyl, benzyl or unsubstituted or substituted phenyl, z1 stands for 0, 1, 2, 3, 4 or 5, $A_1$ stands for a unsubstituted or substituted divalent aromatic radical, or (b) a mixture of benzoic derivatives (A1) and (A2)

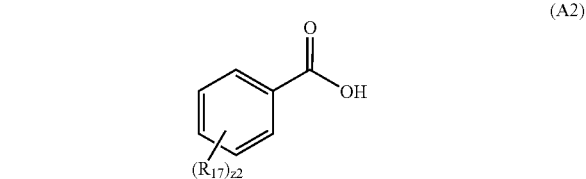

is raected with a dihalogen derivative of formula (B1), wherein $R_{17}$, different from $R_{16}$, stands for —OH, unsubstituted or substituted $C_1$-$C_8$alkyl, unsubstituted or substituted $C_1$-$C_8$alkoxy, unsubstituted or substituted phenyl or naphthyl, —COOR$_{1a}$, —C(O)R$_{1a}$, or —NR$_{1a}$R$_{1b}$, z2 stands for 0, 1, 2, 3, 4 or 5, or (c) benzoic acid derivative of formula (A1) is reacted with dihalogen derivative (B1) to yield compound (C1)

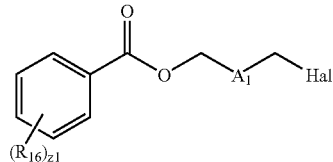

(C1)

and then compound (C1) is reacted with compound of formula (A2), wherein the molar ratio of (A1) or ((A1)+(A2)) to (B1) is chosen in the range of from 3:1 to 10:1.

If desired, compound (C1) can be isolated and used for further reactions such as with compound (A1) or (A2), or—in order to obtain compounds (2) or (2a)—with compound (1) resp. (1a) in analogy to the following reaction scheme:

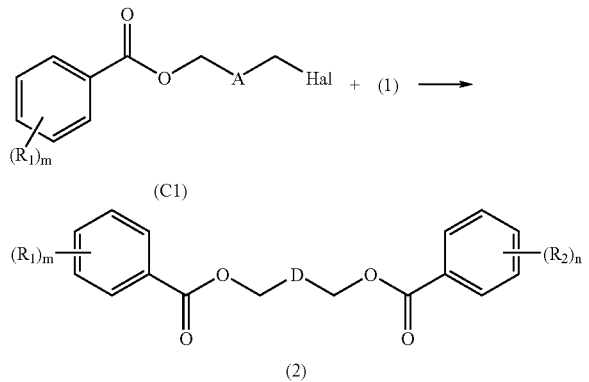

provided $R_1$ and/or $R_2$ of compound (1) stand for hydroxy.

The reaction conditions can be chosen as described for the synthesis of compounds (1) or (1a) above.

Generally, a mixture of compounds (1) resp. (1a) and (2) resp. (2a) can be obtained either by simply mixing the two components or by adjusting the above reaction conditions for the manufacture of (1) in such a way that compounds (1) resp. (1a) and (2) resp. (2a) are produced during the same reaction. Preferably this can be done, if the amounts of (A1) and (B1) or ((A1)+(A2) are chosen such that the molar ratios (A1) to (B1) or ((A1)+(A2) to (B1) are in the range of less than 3:1, preferably from 0.01:1 to 2:1. Of course, an optimisation of the usual process parameters such as temperature, molar ratio, solvent, duration etc. also could lead to the inventive mixture as can be seen in the examples.

Therefore, another embodiment of the present invention relates to a process for the manufacture of a mixture of colour developer (1) and compound of formula (2), in which
(a) benzoic acid derivative of formula (A1) is reacted with a dihalogen derivative of formula (B1), or
(b) a mixture of benzoic derivatives (A1) and (A2) is reacted with a dihalogen derivative of formula (B1), or
(c) benzoic add derivative of formula (A1) is reacted with dihalogen derivative (B1) to yield compound (C1) and then compound (C1) is reacted with compound of formula (A2), wherein the molar ratio of (A1) or ((A1)+(A2)) to (B1) is chosen in the range of less than 3:1.

Another embodiment of the present invention is directed to a heat sensitive composition consisting of a) a colour forming compound, and
b) a colour developer of the formula (1).

A further embodiment of the present invention is directed to a heat sensitive composition consisting of
a) a colour forming compound, and
b) a mixture of colour developer of formula (1a) and compound of formula (2).

A further embodiment of this invention relates to a mixture of a colour developer of formula (1) and a compound of formula (2), which is obtainable by the process described above.

A further embodiment of this invention relates to a process for the manufacture of compound (2), wherein compound (C1) is reacted with colour developer (1).

The colour forming compounds are, for example, triphenylmethanes, lactones, benzoxazines, spiropyrans or preferably fluorans.

Preferred colour formers include but are not limited to; 3-diethylamino-6-methylfluoran, 3-dimethylamino-6-methyl-7-anilinofluoran, 3-diethylamino-6-methyl-7-anilinofluoran, 3-diethylamino-6-methyl-7-(2,4-dimethylanilino)fluoran, 3-diethylamino-6-methyl-7-chlorofluoran, 3-diethylamino-6-methyl-7-(3-trifluoromethylanilino)fluoran, 3-diethylamino-6-methyl-7-(2-chloroanilino)fluoran, 3-diethylamino-6-methyl-7-(4-chloroanilino)fluoran, 3-diethylamino-6-methyl-7-(2-fluoroanilino)fluoran, 3-diethylamino-6-methyl-7-(4-n-octylanilino)fluoran, 3-diethylamino-7-(4-n-octylanilino)fluoran, 3-diethylamino-7-(n-octylamino)fluoran, 3-diethylamino-7-(dibenzylamino)fluoran, 3-diethylamino-6-methyl-7-(dibenzylamino)fluoran, 3-diethylamino-6-chloro-7-methylfluoran, 3-diethylamino-7-t-butylfluoran, 3-diethylamino-7-carboxyethylfluoran, 3-diethylamino-6-chloro-7-anilinofluoran, 3-diethylamino-6-methyl-7-(3-methylanilino)fluoran, 3-diethylamino-6-methyl-7-(4-methylanilino)fluoran, 3-diethylamino-6-ethoxyethyl-7-anilinofluoran, 3-diethylamino-7-methylfluoran, 3-diethylamino-7-chlorofluoran, 3-diethylamino-7-(3-trifluoromethylanilino)fluoran, 3-diethylamino-7-(2-chloroanilino)fluoran, 3-diethylamino-7-(2-fluoroanilino)fluoran, 3-diethylamino-benzo[a]fluoran, 3-diethylamino-benzo[c]fluoran, 3-dibutylamino-7-dibenzylaminofluoran, 3-dibutylamino-7-anilinofluoran, 3-diethylamino-7-anilinofluoran, 3-dibutylamino-6-methyl fluoran, 3-dibutylamino-6-methyl-7-anilinofluoran, 3-dibutylamino-6-methyl-7-(2,4-dimethylanilino)fluoran, 3-dibutylamino-6-methyl-7-(2-chloroanilino)fluoran, 3-dibutylamino-6-methyl-7-(4-chloroanilino)fluoran, 3-dibutylamino-6-methyl-7-(2-fluoroanilino)fluoran, 3-dibutylamino-6-methyl-7-(3-trifluoromethylanilino)fluoran, 3-dibutylamino-6-ethoxyethyl-7-anilinofluoran, 3-dibutylamino-6-chloroanilinofluoran, 3-dibutylamino-6-methyl-7-(4-methylanilino)fluoran, 3-dibutylamino-7-(2-chloroanilino)fluoran, 3-dibutylamino-7-(2-fluoroanilino)fluoran, 3-dibutylamino-7-(N-methyl-N-formylamino)fluoran, 3-dipentylamino-6-methyl-7-anilinofluoran, 3-dipentylamino-6-methyl-7-(4-2-chloroanilino)fluoran, 3-dipentylamino-7-(3-trifluoromethylanilino)fluoran, 3-dipentylamino-6-chloro-7-anilinofluoran, 3-dipentylamino-7-(4-chloroanilino)fluoran, 3-pyrrolidino-6-methyl-7-anilinofluoran, 3-piperidino-6-methyl-7-anilinofluoran, 3-(N-methyl-N-propylamino)methyl-7-anilinofluoran, 3-(N-methyl-N-cyclohexylamino)-6-methyl-7-anilinofluoran, 3-(N-ethyl-N-cyclohexylamino)-6-methyl-7-anilinofluoran, 3-(N-ethyl-p-toluidino)-6-methyl-7-anilinofluoran, 3-(N-ethyl-N-isoamylamino)-6-methyl-7-anilinofluoran, 3-(N-ethyl-N-isoamylamino)-6-chloro-7-anilinofluoran, 3-(N-ethyl-N-tetrahydrofurfurylamino)-6-methyl-7-anilinofluoran, 3-(N-ethyl-N-isobutylamino-6- methyl-7-anilinofluoran, 3-(N-butyl-N-isoamylamino)-6-methyl-7-anilinofluoran, 3-(N-isopropyl-N-3-pentylamino)-6-methyl-7-anilinofluoran, 3-(N-ethyl-N-ethoxypropylamino)-6-methyl-7-anilinofluoran, 3-cyclohexylamino-6-chlorofluoran, 2-methyl-6-p-(p-dimethylaminophenyl)aminoanilinofluoran, 2-methoxy-6-p-(p-dimethylaminophenyl)aminoanilinofluoran, 2-chloro-3-methyl-p-p-phenylamino-phenyl)aminoanilinofluoran, 2-diethylamino-6-p-(p-dimethylaminophenyl)aminoanilinofluoran, 2-phenyl-6-methyl-6-p-(p-phenylaminophenyl)aminoanilinofluoran, 2-benzyl-6-p-(p-phenylaminophenyl)aminoanilinofluoran, 3-methyl-6-p-(p-dimethylaminophenyl)aminoanilinofluoran, 3-diethylamino-6-p-(p-diethylaminophenyl)aminoanilinofluoran, 3-diethylamino-6-p-(p-dibutylaminophenyl)aminoanilinofluoran, 2,4-dimethyl-6-[(4-dimethylamino)-anilino]fluoran, 3-[(4-dimethylaminophenyl)amino]-5,7-dimethylfluoran, 3,6,6'-tris(dimethylamino)spiro[fluorene-9,3'-phthalide], 3,6,6'-tris(diethylamino)spiro[fluorene-9,3'-phthalide], 3,3-bis(p-dimethylaminophenyl)-6-dimethylaminophthalide, 3,3-bis(p-dimethylaminophenyl)phthalide, 3,3-bis-[2-(p-dimethylaminophenyl)-2-(p-methoxyphenyl)ethenyl-4,5,6,7-tetrabromophthalide, 3,3-bis[2-(p-dimethylaminophenyl)-2-(p-methoxyphenyl)ethenyl-4,5,6,7-tetrachlorophthalide, 3,3-bis[1,1-bis(4-pyrrolidinophenyl)ethylene-2-yl]-4,5,6,7-tetrabromophthalide, 3,3-bis-[1-(4-methoxyphenyl)-1-(4-pyrridinophenyl)ethylene-2-yl]-4,5,6,7-tetrachlorophthalide, 3-(4-diethylamino-2-ethoxyphenyl)-3-(1-ethyl-2-methylindole-3-yl)-4-azaphthalide, 3-(4-diethylamino-2-ethoxyphenyl)-3-(1-octyl-2-methylindole-3-yl)-4-azaphthalide, 3-(4-cyclohexylethylamino-2-methoxyphenyl)-3-(1-ethyl-2-methylindole-3-yl)-4-azaphthalide, 3,3-bis(1-ethyl-2-methylindole-3-yl)phthalide, 3,3-bis(1-octyl-2-methylindole-3-yl)phthalide, mixture of 2-phenyl-4-(4-diethylaminophenyl)-4-(4-methoxyphenyl)-6-methyl-7-dimethylamino-3,1-benzoxazine and 2-phenyl-4-(4-diethylaminophenyl-4-(4-methoxyphenyl)-8-methyl-7-dimethylamino-3,1-benzoxazine, 4,4'-[1-methylethylidene)bis(4,1-phenyleneoxy-4,2-quinazolinediyl)]bis[N,N-diethylbenzenamine], bis(N-methyldiphenylamine)-4-yl-(N-butylcarbazole)-3-yl-methane, 6-diethylamino-1,2-benzofluoran, 3-diethylamino)-6,8-dimethylfluoran, 3-N-etyhl-N-p-methylphenylamino-7-methylfluoran and mixtures thereof.

All of the above colour forming compounds can be used singly or as a mixture with other colour forming compounds; or they may also be used together with further black colour forming compounds.

Highly preferred are 3-diethylamino-6-methyl-7-anilinofluoran, 3-diethylamino-6-methyl-7-(3-methylanilino)fluoran, 3-diethylamino-6-methyl-7-(2,4-dimethylanilino)fluoran, 3-dibutylamino-6-methyl-7-anilinofluoran, 3-dipentylamino-6-methyl-7-anilinofluoran, 3-(N-methyl-N-propylamino)-6-methyl-7-anilinofluoran, 3-(N-methyl-N-cyclohexylamino)-6-methyl-7-anilinofluoran, 3-(N-ethyl-N-isoamylamino)-6-methyl-7-anilinofluoran, 3-diethylamino-6-chloro-7-anilinofluoran, 3-dibutylamino-7-(2-chloroanilino)fluoran, 3-N-ethyl-p-toluidino-6-methyl-7-anilinofluoran, 3-(N-ethyl-N-tetrahydrofurfurylamino)-6-methyl-7-anilinofluoran, 3-(N-ethyl-N-isobutylamino)-6-methyl-7-anilinofluoran, 3-N-ethyl-N-ethoxypropylamino-6-methyl-7-anilinofluoran, 2,4-dimethyl-6-[(4-dimethylamino)anilino]fluoran, 3-(4-diethylamino-2-ethoxyphenyl)-3-(1-octyl-2-methylindole-3yl)-4-azaphthalide, 3,3-bis(p-dimethylaminophenyl)-6-dimethylaminophthalide and mixtures thereof.

It is also possible to use solid solutions comprising at least two colour forming compounds.

A monophase (or single-phase or guest-host) solid solution possesses a crystal lattice which is identical with the crystal lattice of one of its components. One component is embedded as the 'guest' in the crystal lattice of the other component, which acts as the 'host'. The X-ray diffraction pattern of such a monophase solid solution is substantially identical to that of one of the components, called the 'host'. Within certain limits, different proportions of the components produce almost identical results.

In the literature, the definitions by the various authors, such as, G. H. Van't Hoff, A. I. Kitaigorodsky and A. Whitacker for solid solutions and mixed crystals are often contradictory, (cf, e.g. 'Analytical Chemistry of Synthetic Dyes', Chapter 10/page 269, Editor K. Venkataraman, J. Wiley, New York, 1977).

The term 'monophase solid solution' or 'multiphase solid solution' or mixed crystal', as defined herein, therefore, should be taken from the following definitions, which have been adapted to the current improved state of knowledge of such systems: A monophase (or single-phase or guest-host) solid solution possesses a crystal lattice, which is identical with the crystal lattice of one of its components. One component is embedded as the 'guest' in the crystal lattice of the other component, which acts as the 'host'. The X-ray diffraction pattern of such a monophase solid solution is substantially identical to that of one of the components, called the 'host'. Within certain limits, different proportions of the components produce almost identical results.

A multiphase solid solution possesses no precise, uniform crystal lattice. It differs from a physical mixture of its components in that the crystal lattice of at least one of its components is partially or completely altered. In comparison to a physical mixture of the components, which gives an X-ray diffraction diagram that is additive of the diagrams seen for the individual components. The signals in the X-ray diffraction diagram of a multiphase solid solution are broadened, shifted or altered in intensity. In general, different proportions of the components produce different results.

A mixed crystal (or solid compound type) solid solution possesses a precise composition and a uniform crystal lattice, which is different from the crystal lattices of all its components. If different proportions of the components lead, within certain limits, to the same result, then a solid solution is present in which the mixed crystal acts as a host.

For the avoidance of doubt it may also be pointed out that, inter alia, there may also be amorphous structures and mixed aggregates consisting of different particles of different physical type, such as, for example, an aggregate of different components each in pure crystal modification. Such amorphous structures and mixed aggregates cannot be equated with either solid solutions or mixed crystals, and possess different fundamental properties.

As hereinbefore detailed, the monophase solid solutions comprise a plurality of colour compounds. Suitable colour forming materials, which may be included in the solid solutions are those given above.

Of particular interest are the following monophase solid solutions:
3-dibutylamino-6-methyl-7-anilinofluoran and 3-dibutylamino-7-dibenzylaminofluoran; 3-dibutylamino-6-methyl-7-anilinofluoran and 3-dibutylamino-7-anilinofluoran; 3-dibutylamino-6-methyl-7-anilinofluoran and 3-diethylamino-7-anilinofluoran; 3-diethylamino-6-methyl-7-anilinofluoran and 3-diethylamino-7-anilinofluoran; 3-dibutylamino-6-methyl-7-anilinofluoran and 3-diethylamino-6-methyl-7-anilinofluoran; 3-dibutylamino-6-methyl-7-anilinofluoran and 3-N-isoamyl-N-ethylamino-6-methyl-7-anilinofluoran; 3-dibutylamino-6-methyl-7-anilinofluoran and 3-N-2-pentyl-N-ethylamino-6-methyl-7-anilinofluoran; 3-dibutylamino-6-methyl-7-anilinofluoran and 3-N-isopropyl-N-ethylamino-6-methyl-7-anilinofluoran; 3-dibutylamino-6-methyl-7-anilinofluoran and 3-N-Cyclohexylmethyl-N-ethylamino-6-methyl-7-anilinofluoran; 3-dibutylamino-6-methyl-7-anilinofluoran and 3-dipropylamino-6-methyl-7-anilinofluoran; 3-dibutylamino-6-methyl-7-anilinofluoran and 3-N-2-butyl-N-ethylamino-6-methyl-7-anilinofluoran; 3-dibutylamino-6-methyl-7-anilinofluoran and 3-N-cyclohexyl-N-methylamino-6-methyl-7-anilinofluoran; 3-dibutylamino-6-methyl-7-anilinofluoran and 3-diethylamino-6-methyl-7-(3-methylanilino)fluoran; 3-dibutylamino-6-methyl-7-anilinofluoran and 3-diethylamino-6-methyl-7-(2,4-dimethylanilino)fluoran; 3-dibutylamino-6-methyl-7-anilinofluoran and 3-dipentylamino-6-methyl-7-anilinofluoran; 3-dibutylamino-6-methyl-7-anilinofluoran and 3-(N-methyl-N-propylamino)-6-methyl-7-anilinofluoran; 3-dibutylamino-6-methyl-7-anilinofluoran and 3-diethylamino-6-chloro-7-anilinofluoran; 3-dibutylamino-6-methyl-7-anilinofluoran and 3-dibutylamino-7-(2-chloroanilino)fluoran; 3-dibutylamino-6-methyl-7-anilinofluoran and 3-N-ethyl-p-toluidino-6-methyl-7-anilinofluoran; 3-dibutylamino-6-methyl-7-anilinofluoran and 3-(N-ethyl-N-tetrahydrofurfurylamino)-6-methyl-7-anilinofluoran; 3-dibutylamino-6-methyl-7-anilinofluoran and 3-(N-ethyl-N-isobutylamino)-6-methyl-7-anilinofluoran; 3-dibutylamino-6-methyl-7-anilinofluoran and 3-N-ethyl-N-ethoxypropylamino-6-methyl-7-anilinofluoran; 3-dibutylamino-6-methyl-7-anilinofluoran and 2,4-dimethyl-6-[(4-dimethylamino)anilino]fluoran; 3-N-isoamyl-N-ethylamino-6-methyl-7-anilinofluoran and 3-diethylamino-6-methyl-7-anilinofluoran; 3-diethylamino-6-methyl-7-anilinofluoran and 3-N-propyl-N-methylamino-6-methyl-7-anilinofluoran; 3-diethylamino-6-methyl-7-(3-tolyl)aminofluoran and 3-diethylamino-6-methyl-7-anilinofluoran; 3-dibutylamino-6-methyl-7-anilinofluoran and 3,3-bis(1-octyl-2-methylindol-3-yl)phthalide; 3-dibutylamino-6-methyl-7-anilinofluoran and mixture of 2-phenyl-4-(4-diethylaminophenyl)-4-(4-methoxyphenyl)-6-methyl-7-dimethylamino-3,1-benzoxazine and 2-phenyl-4-(4-diethylaminophenyl)-4-(4-methoxyphenyl)-8-methyl-7-dimethylamino-3,1-benzoxazine; 3-dibutylamino-6-methyl-7-anilinofluoran and 4,4'-[1-methylethylidene)bis(4,1-phenyleneoxy-4,2-uinazolinediyl)]bis[N,N-diethylbenzenamine].

In the above monophase solid solutions the first compound is in a molar ratio of 75 to 99.9% by mole, the second compound is in a ratio of 25 to 0.1% by mole.

Examples of monophase solid solutions comprising two components A and B in the stated ratios are: 3-dibutylamino-6-methyl-7-anilinofluoran (99.9%), 3-diethylamino-6-methyl-7-anilinofluoran (0.1%); 3-dibutylamino-6-methyl-7-anilinofluoran (99%), 3-diethylamino-6-methyl-7-anilinofluoran (1%); 3-dibutylamino-6-methyl-7-anilinofluoran (95%), 3-diethylamino-6-methyl-7-anilinofluoran (5%); 3-dibutylamino-6-methyl-7-anilinofluoran (90%) and 3-N-2-pentyl-N-ethylamino-6-methyl-7-anilinofluoran (10%); 3-dibutylamino-6-methyl-7-anilinofluoran (95%) and 3-N-2-pentyl-N-ethylamino-6-methyl-7-anilinofluoran (5%); 3-dibutylamino-6-methyl-7-anilinofluoran (90%) and 3-N-isopropyl-N-ethylamino-6-methyl-7-anilinofluoran (10%); 3-dibutylamino-6-methyl-7-anilinofluoran (95%) and 3-N-isopropyl-N-ethylamino-6-methyl-7-anilinofluoran (5%); 3-dibutylamino-6-methyl-7-anilinofluoran (90%) and 3-N-Cyclohexylmethyl-N-ethylaminomethyl-6-methyl-7-anilinofluoran (10%); 3-dibutylamino-6 methyl-7-anilinofluoran (95%) and 3-N-Cyclohexylmethyl-N-ethylamino-6-methyl-7-anilinofluoran (5%); 3-dibutylamino-6-methyl-7-anilinofluoran (90%) and 3-dipropylamino-6-methyl-7-anilinofluoran (10%); 3-dibutylamino-6-methyl-7-anilinofluoran (95%) and 3-dipropylamino-6-methyl-7-anilinofluoran (5%); 3-dibutylamino-6-methyl-7-anilinofluoran (90%) and 3-N-2-butyl-N-ethylaminomethyl-6-methyl-7-anilinofluoran (10%); 3-dibutylamino-6-methyl-7-anilinofluoran (95%) and 3-N-2-butyl-N-ethylamino-6-methyl-7-anilinofluoran (5%); 3-dibutylamino-6-methyl-7-anilinofluoran (90%), 3-diethylamino-6-methyl-7-anilinofluoran (10%); 3-dibutylamino-6-methyl-7-anilinofluoran (85%), 3-diethylamino-6-methyl-7-anilinofluoran (15%); 3-dibutylamino-6-methyl-7-anilinofluoran (80%), 3-diethylamino-6-methyl-7-anilinofluoran (20%); 3-dibutylamino-6-methyl-7-anilinofluoran (95%), 3-N-isoamyl-N-ethylamino-6-methyl-7-anilinofluoran (5%); 3-dibutylamino-6-methyl-7-anilinofluoran (90%), 3-N-isoamyl-N-ethylamino-6-methyl-7-anilinofluoran (10%); 3-dibutylamino-6-methyl-7-anilinofluoran (80%), 3-N-isoamyl-N-ethylamino-6-methyl-7-anilinofluoran (20%); 3-dibutylamino-6-methyl-7-anilinofluoran (90%), 3-N cyclohexyl-N-methylamino-6-methyl-7-anilinofluoran (10%); 3-diethylamino-6-methyl-7-anilinofluoran (90%), 3-N-isoamyl-N-methylamino-6-methyl-7-anilinofluoran (10%); 3-diethylamino-6-methyl-7-anilinofluoran (80%), 3-N-isoamyl-N-ethylamino-6-methyl-7-anilinofluoran (20%); 3-diethylamino-6-methyl-7-anilinofluoran (20%), 3-N-isoamyl-N-ethylamino-6-methyl-7-anilinofluoran (80%); 3-diethylamino-6-methyl-7-anilinofluoran (10%), 3-N-isoamyl-N-ethylamino-6-methyl-7-anilinofluoran (90%); 3-diethylaminomethyl-7-anilinofluoran (90%), 3-N-propyl-N-methylamino-6-methyl-7-anilinofluoran (10%); 3-diethylamino-6-methyl-7-anilinofluoran (80%), 3-N-propyl-N-methylamino-6-methyl-7-anilinofluoran (20%); 3-diethylamino-6-methyl-7-anilinofluoran (20%), 3-N-propyl-N-methylamino-6-methyl-7-anilinofluoran (80%); 3-diethylamino-6-methyl-7-anilinofluoran (10%), 3-N-propyl-N-methylamino-6-methyl-7-anilinofluoran (90%); 3-diethylamino-6-methyl-7-anilinofluoran (10%), 3-diethylamino-6-methyl-7-(3-tolyl)aminofluoran (90%); 3-diethylamino-6-methyl-7-anilinofluoran (20%), 3-diethylamino-6-methyl-7-(3-tolyl)aminofluoran (80%); 3-dibutylamino-6-methyl-7-anilinofluoran (90%), 3,3-bis(1-octyl-2-methylindol-3-yl)phthalide (10%); 3-dibutylamino-6-methyl-7-anilinofluoran (80%), 3,3-bis(1-octyl-2-methylindol-3-yl)phthalide(20%); 3-dibutylamino-6-methyl-7-anilinofluoran (90%), mixture of 2-phenyl-4-(4-diethylaminophenyl)-4-(4-methoxyphenyl)-6-methyl-7-dimethylamino-3,1-benzoxazine and 2-phenyl-4-(4-diethylaminophenyl)-4-(4-methoxyphenyl)-8-methyl-7-dimethylamino-3,1-benzoxazine(10%); 3-dibutylamino-6-methyl-7-anilinofluoran (80%), mixture of 2-phenyl-4-(4-diethylaminophenyl)-4-(4-methoxyphenyl)-6-methyl-7-dimethylamino-3,1-benzoxazine and 2-phenyl-4-(4-diethylaminophenyl)-4-(4-methoxyphenyl)-8-methyl-7-dimethylamino-3,1-benzoxazine(20%); 3-dibutylamino-6-methyl-7-anilinofluoran (90%), 4,4'-[1-methylethylidene)bis(4,1-phenyleneoxy-4,2-quinazolinediyl)]bis[N,N-diethylbenzenamine](10%); 3-dibutylamino-6-methyl-7-anilinofluoran (80%), 4,4'-[1-methylethylidene)bis(4,1-phenyleneoxy-4,2-quinazolinediyl)]bis[N,N-diethylbenzenamine](20%).

The monophase solid solutions can be used singly or as a mixture with other colour forming compounds such as triphenylmethanes, lactones, fluorans, benzoxazines and spiropyrans; or they may also be used together with further black colour forming compounds. Examples of such other colour forming compounds are given hereinbefore.

The monophase solid solutions can be prepared by a variety of methods. One such method is the recrystallisation method wherein a physical mixture of the desired components is dissolved, with or without heating, in a suitable solvent or solvent mixture. Suitable solvents include but are not limited to toluene, benzene, xylene, dichlorobenzene, chlorobenzene, 1,2-dichloroethane, methanol, ethanol, isopropanol, n-butanol, acetonitrile, dimethylformamide or mixtures of these solvents with each other and with water. The monophase solid solution is then isolated by crystallisation from the solvent or solvent mixture. This can be brought about by cooling, standing, addition of a further solvent to promote crystallisation or concentration by standard means such as distillation, steam distillation and vacuum distillation. When the monophase solid solution is isolated by concentration it may be advantageous to do so in the presence of a small amount of base, to improve the visual aspect of the isolated product.

Alternatively, monophase solid solutions can be prepared from mixtures of the appropriate starting materials. The technique can be used to produce mixtures of two or more fluorans or phthalides. For example, mixtures of two fluorans are produced by replacing a single starting material with two analogous materials to the same total molar concentration in the reaction. In the case of fluorans, these starting materials are derivatives of amino phenols, phthalic anhydrides, keto acids and diphenylamines.

Usually, the molar ratio of colour developer or colour developers to colour forming compound or compounds is chosen in the range of from 20:1 to 0.1:1, preferably from 5:1 to 0.5:1, more preferably from 4:1 to 1:1.

In addition to the inventive colour developers (1), (1a) and (2), I is possible to further add additional colour developers. Such developers are exemplifed by but not limited to: N-p-toluenesulfonyl-N'-3-(p-toluenesulfonyloxy)phenyl urea, 4,4'-isopropylidene bisphenol, 4,4'-sec-butylidene bisphenol, 4,4'-cyclohexylidene bisphenol, 2,2-bis-(4-hydroxyphenyl)-4-methylpentane, 2,2-dimethyl-3,3-di(4-hydroxyphenyl)butane, 2,2'-dihydroxydiphenyl, 1-phenyl-1,1-bis(4-hydroxyphenyl)butane, 4-phenyl-2,2-bis(4-hydroxyphenyl)butane, 1-phenyl-2,2-bis(4-hydroxyphenyl)butane, 2,2-bis(4'-hydroxy-3'-methylphenyl)-4-methylpentane, 2,2-bis(4'-hydroxy-3'-tert-butyllphenyl)-4-methylpentane, 4,4'-sec-butylidene-bis(2-methylphenol), 4,4'-isopropylidene-bis(2-tert-butylphenol), 2,2-bis(4'-hydroxy-3'-isopropylphenyl)-4-methylpentane, allyl-4,4-bis(4'-hydroxyphenyl)pentanoate, propargyl-4,4-bis(4-hydroxyphenyl)pentanoate, n-propyl-4,4-bis(4'-hydroxyphenyl)pentanoate, 2,4-bis(phenylsulfonyl) phenol, 2-(4-methylsulfonyl)-4-(phenylsulfonyl)phenol, 2-(phenylsulfonyl)-4-(4-methylsulfonyl)phenol, 2,4-bis(4-methylphenylsulfonyl)phenol, pentamethylene-bis(4-hydroxybenzoate), 2,2-dimethyl-3,3-di(4-hydroxyphenyl)pentane, 2,2-di(4-hydroxyphenyl)hexane, 4,4'-dihydroxydiphenyl thioether, 1,7-di(4-hydroxyphenylthio)-3,5-dioxaheptane, 2,2'-bis(4-hydroxyphenylthio)diethyl ether, 4,4'-dihydroxy-3,3'-dimethylphenyl thioether; benzyl-4-hydroxybenzoate, ethyl-4-hydroxybenzoate, propyl-4-hydroxybenzoate, isopropyl-4-hydroxybenzoate, butyl-4-hydroxybenzoate, isobutyl-4-hydroxybenzoate, 4,4'-dihydroxydiphenyl sulfone, 2,4'-dihydroxydiphenyl sulfone, 4-hydroxy-4'-methyldiphenyl sulfone, 4-hydroxy-4'-isopropoxydiphenyl sulfone, 4-hydroxy-4'-butoxydiphenyl sulfone, 4,4'-dihydroxy-3,3'-diallyldiphenyl sulfone, 3,4-dihydroxy-4'-methyldiphenyl sulfone, 4,4'-dihydroxy-3,3',5,5'-tetrabromodiphenyl sulfone, 4,4'-bis(p-toluenesulphonylaminocarbonylamino)diphenylmethane, N-p-toluenesulphonyl-N'-phenyl urea, dimethyl 4-hydroxyphthalate, dicyclohexyl 4-hydroxyphthalate, diphenyl 4-hydroxyphthalate, 4-[2-(4-methoxyphenyloxy)ethyloxy]salicylate, 3,5-di-tert-butylsalicylic acid, 3-benzyl salicylic acid, 3-($\alpha$-methylbenzyl)salicylic acid, 3-phenyl-5-($\alpha,\alpha$-dimethylbenzyl)salicylic acid, 3,5-di-$\alpha$-methylbenzyl salicylic acid; metal salts of salicylic acid, 2-benzylsulfonylbenzoic acid, 3-cyclohexyl-4-hydroxybenzoic acid, zinc benzoate, zinc 4-nitrobenzoate, 4-(4'-phenoxybutoxy)phthalic acid, 4-(2'-phenoxyethoxy)phthalic acid, 4-(3'-phenylpropyloxy)phthalic acid, mono(2-hydroxyethyl)-5-nitro-isophthalic acid, 5-benzyloxycarbonyl isophthalic acid, 5-(1'-phenylethanesulfonyl)isophthalic acid, bis(1,2-dihydro-1,5-dimethyl-2-phenyl-3H-pyrazol-3-one-O)bis(thiocyanato-N) zinc, polymer of 4,4'-sulfonylbis-phenol with 1,1'-oxybis[2-chloroethane](CAS [191680-83-8]), polymer of 2,2-bis(hydroxymethyl)1,3-propanediol with 4-hydroxybenzoate (CAS [92881-24-8]), polymeric esters of 4-hydroxybenzoic acid (formed by the reaction of 4-hydroxybenzoic acid with polyhydroxy compounds), N-(4-hydroxyphenyl)-4'-methylbenzenesulfonamide, zinc 4-(octyloxycarbonylamino)salicylate, urea urethane developers as described in EP-A 1,116,713, or polyhydroxystyrene as decribed e.g. in US 2003/50191, and mixtures thereof.

Preferably, the inventive heat sensitive composition is used for the manufacture of a heat sensitive recording material.

Hence, another embodiment of this invention relates to a heat sensitive recording material, which comprises at least one colour developer of formula (1) resp. (1a), or the inventive composition, i.e. a mixture of colour developer of formula (1) or (1a) and compound (2) resp. (2a).

In another preferred embodiment, the heat sensitive recording material further comprises at least one sensitiser. In still another preferred embodiment, the heat sensitive recording material further comprises at least one stabiliser, and/or further additives as described below.

The heat sensitive recording material can be prepared according to conventional methods. For example, at least one colour forming compound, at least one colour developer and, if desired, at least one sensitiser are pulverised separately in water or a suitable dispersing medium, such as aqueous polyvinyl alcohol by means of e.g. a ball mill, an attritor, a sand mill, a bead mill or like pulverizer to form an aqueous or other dispersion with an average particle diameter preferably in the range of 0.2 to 2.0 µm.

The fine particle dispersions thus obtained are usually combined and then mixed with conventional amounts of binder, pigment, and, if desired, a stabiliser and/or one or more auxiliaries, and the resulting mixture preferably is stirred to obtain a heat sensitive coating composition. This compositions is usually then applied to a support and the resulting coating is dried.

The inventive system can be employed for other end use applications using colour-forming materials, for example, a temperature indicating material.

The support can be a variety of suitable supports used in this field, and examples thereof include paper, wood-free paper made from non-chlorine bleached pulp, base paper containing waste paper, plastic films, and synthetic paper.

In addition, the heat sensitive recording material of the invention can contain a sensitiser. Generally, the molar ratio of sensitizer to colour former is chosen in the range of from 0.5:1 to 10:1, preferably 1:1 to 4:1.

Representative examples of sensitiser are stearamide, methylol stearamide, p-benzylbiphenyl, m-terphenyl, 2-benzyloxynaphthalene, 4-methoxybiphenyl, dibenzyl oxalate, di(4-methylbenzyl)oxalate, di(4-chlorobenzyl)oxalate, dimethyl phthalate, dibenzyl terephthalate, dibenzyl isophthalate, 1,2-diphenoxyethane, 1,2-bis(4-methylphenoxy)ethane, 1,2-bis(3-methylphenoxy)ethane, 4,4'-dimethylbiphenyl, phenyl-1-hydroxy-2-naphthoate, 4-methylphenyl biphenyl ether, 1,2-bis(3,4-dimethylphenyl)ethane, 2,3,5,6-4'-methyldiphenyl methane, 1,4-diethoxynaphthalene, 1,4-diacetoxybenzene, 1,4-diproprionoxybenzene, o-xylylene-bis(phenyl ether), 4-(m-methylphenoxymethyl)biphenyl, p-hydroxyacetanilide, p-hydroxybutyranilide, p-hydroxynonananilide, p-hydroxylauranilide, p-hydroxyoctadecananilide, N-phenyl-phenylsulphonamide, acetyl biphenyl compounds (e.g. as described in JP2003 063149A2) and 2-phenoxyethyl-N-phenylcarbamate.

The above sensitisers are known or can be prepared according to known methods.

In addition, the heat sensitive recording material of the invention can contain a stabiliser. As a rule, the molar ratio of stabilizer to colour former is chosen in the range of from 0.05:1 to 10:1, preferably from 0.1:1 to 2:1.

Representative stabilisers for use in heat sensitive recording materials include 2,2'-methylene-bis(4-methyl-6-tert-butylphenol), 2,2'-methylene-bis(4-ethyl-6-tert-butylphenol), 4,4'-butylidene-bis(3-methyl-6-tert-butylphenol), 4,4'-thiobis(2-tert-butyl-5-methylphenol), 1,1,3-tris(2-methyl-4-hydroxy-5-tert-butylphenyl)butane, 1,1,3-tris(2-methyl-4-hydroxy-5-cyclohexylphenyl) butane, bis(3-tert-butyl-4-hydroxy-6-methylphenyl)sulfone, bis(3,5-dibromo-4-hydroxyphenyl)sulfone, 4,4'-sulfinyl bis(2-tert-butyl-5-methylphenol), 2,2'-methylene bis (4,6-di-tert-butylphenyl) phosphate and alkali metal, ammonium and polyvalent metal salts thereof, 4-benzyloxy-4'-(2-methylglycidyloxy)diphenyl sulfone, 4,4'-diglycidyloxydiphenyl sulfone, 1,4-diglycidyloxybenzene, 4-[α-(hydroxymethyl)benzyloxy]-4-hydroxydiphenyl sulfone, metal salts of p-nitrobenzoic acid, metal salts of phthalic acid mono benzyl ester, metal salts of cinnamic acid, 2,2',3,3'-tetrahydro-3,3,3',3'-tetramethyl-1,1'-spribi-(1H-indene)-6,6'-diol and mixtures thereof.

Preferred stabilisers are 4,4'-butylidene-bis(3-methyl-6-tert-butylphenol), 4,4'-thio-bis(2-tert-butyl-5-methylphenol), 1,1,3-tris(2-methyl-4-hydroxy-5-tert-butylphenyl)butane, 1,1,3-tris(2-methyl-4-hydroxy-5-cyclohexylphenyl) butane, 4-benzyloxy-4'-2-methylglycidyloxy)diphenyl sulfone and mixtures thereof.

Representative binders for use in the heat sensitive recording layer include polyvinyl alcohol (fully or partially hydrolysed), carboxy-modified polyvinyl alcohol, acetoacetyl-modified polyvinyl alcohol, diacetone-modified polyvinyl alcohol, silicon-modified polyvinyl alcohol, oxidised starch, gelatine, caesin, derivatives of cellulose such as hydroxyethyl cellulose, methyl cellulose, ethyl cellulose, carboxymethyl cellulose and acetyl cellulose, starch-vinyl acetate graft copolymers, styrene-maleic anhydride copolymers, methyl vinyl ether-maleic anhydride copolymers, isopropylene-maleic anhydride copolymers and like water-soluble resins, styrene-butadiene latex, acrylic latex, urethane latex and like water-dispersible resins and mixtures thereof. The amount of the binder to be used is about 5 to 40 weight %, preferably about 7 to 30% based on the heat sensitive recording layer.

Representative pigments for use in the heat sensitive recording layer include ground calcium carbonate, precipitated calcium carbonate, kaolin, calcined kaolin, aluminium hydroxide, talc, titanium dioxide, zinc oxide, amorphous silica, barium sulfate, polystyrene resin, urea-formaldehyde resin, hollow plastic pigment and mixtures thereof. As a rule the amount of pigment to be used is chosen in the range of from 5 to 75 weight-%, preferably from 10 to 60 weight-%, based on the heat sensitive recording layer.

Representative lubricants for use in the heat sensitive recording layer include stearamide, methylene bis stearamide, polyethylene wax, carnauba wax, paraffin wax, zinc stearate, calcium stearate and mixtures thereof.

Examples of various auxiliaries that can be added to the heat sensitive layer coating composition, if so desired, include surfactants such as sodium dioctylsulfosuccinate, sodium dodecybenzenesulfonate, sodium lauryl sulfate and fatty acid metal salts; insolubilisers such as glyoxal, urea-formaldehyde resins, melamine-formaldehyde resins, polyamide resins, polyamideamine-epichlorohydrin resins, adipic acid dihydrazide, boric acid, borax, ammonium zirconium carbonate and potassium zirconium carbonate; antifoaming agents, fluorescent whitening agents, fluorescent dyes and/or pigments, tinting dyes and UV absorbers.

Usually the heat sensitive recording layer coating composition is applied to the support in an amount in the range of from 1 to 10 g/m$^2$, preferably from 2 to 7 g/m$^2$ on a dry weight basis. The heat sensitive recording layer coating composition may be applied to the support by a known coating device such as a coating bar, a roll coater, an air knife coater, a blade coater, a gravure coater, a die coater or a curtain coater.

If desired, an undercoat layer can also be provided between the support and the heat sensitive recording layer in order to improve the thermal sensitivity and efficiency during recording. The undercoat layer is formed by coating the support with an undercoat layer coating composition comprising as main components organic hollow particles and/or an oil absorbing pigment and a binder and then drying the coating.

Representative examples of oil absorbing pigments include clay, calcined clay, amorphous silica, precipitated calcium carbonate and talc. The average pigment diameter may be in the range 0.01 to 5 µm, preferably from 0.02 to 3 µm.

Representative examples of organic hollow particles include particles having a shell made from an acrylic resin, styrene-based resin and vinylidene chloride-based resin and having a void ratio of about 50 to 99%. The outside diameter of the organic hollow particle may be in the range of 0.5 to 10 µm, preferably from 1 to 5 µm.

The organic hollow particles may be expandable hollow particles. A typical example of such expandable hollow particles are microcapsules having an average diameter of 0.1 to 5 µm comprising a vinylidene chloride resin shell and butane gas as fill material. When a support coated with an undercoat layer comprising such expandable hollow particles is subjected to heat treatment the microcapsules may expand to an average particle diameter in the range of e.g. 1 to 30 µm.

When the oil absorbing pigment is used in combination with the organic hollow particles, the combined amount of the two components is preferably chosen in the range of from 40 to 90 weight-%, particularly from 50 to 80 weight-%, based on the undercoat layer.

Preferably, the binder used in the undercoat layer is selected from the binders to be used in the heat sensitive recording layer and particularly preferred examples are styrene-butadiene latex, a polyvinyl alcohol or starch-vinyl acetate copolymer. The amount of binder to be used is chosen e.g. in the range of from 5 to 30 weight-%, particularly 10 to 20 weight-%, based on the undercoat layer.

Generally, the undercoat recording layer coating composition is applied to the support in an amount in the range of from 2 to 20 g/m$^2$, preferably from 4 to 12 g/m$^2$ on a dry weight basis.

If desired, a protective layer may be provided on the heat sensitive recording layer to enhance the resistance of the recorded image to water and chemicals, for example, oils, fats, alcohols, plasticisers and the like to improve the runability during recording. Usually, the protective layer is formed by coating the heat sensitive recording layer with a protective layer coating composition comprising as main components a binder having film-forming ability and optionally, a pigment and/or an insolubiliser and/or a lubricant and then drying the resulting coating film.

Representative examples of the binder to be used in the protective layer coating composition include e.g. polyvinyl alcohol (fully or partially hydrolysed), carboxy-modified polyvinyl alcohol, acetoacetyl-modified polyvinyl alcohol, diacetone-modified polyvinyl alcohol, silicon-modified polyvinyl alcohol, starches, gelatine, caesin, gum arabic, derivatives of cellulose such as hydroxyethyl cellulose, methyl cellulose, ethyl cellulose, carboxymethyl cellulose and acetyl cellulose, starch vinyl acetate graft copolymers, styrene-maleic anhydride copolymers, methyl vinyl ether-maleic anhydride copolymers, isopropylene-maleic anhydride copolymers and like water-soluble resins, styrene-butadiene latex, acrylic latex, urethane latex and like water-dispersible resins and mixtures thereof.

The pigment, insolubiliser, lubricant and, if required, other auxiliaries may be chosen from those above described in the heat sensitive recording layer coating composition.

The protective layer coating composition preferably is applied in an amount in the range of from 0.5 to 10 g/m$^2$, preferably from 1 to 5 g/m$^2$ on a dry weight basis and may be applied with a similar coating device to that used to coat the heat sensitive layer.

It is also possible to provide a protective layer, an adhesive layer and a magnetic layer on the rear side of the support.

In particular the invention provides exceptional resistance to plasticiser, oil and heat ageing whilst showing improved background whiteness.

The following non-limiting examples, illustrate the novel materials of the present invention.

EXAMPLES

Example A

A mixture of 4-hydroxybenzoic acid (6.9 g, 0.05 mol) and tetrabutyl ammonium hydroxide (33 ml, 0.05 mol, 40% b.w. aqueous solution) is stirred in methanol/water (1:1, 60 ml) for 3 hours at room temperature. After the solvent is evaporated, the resulting oil is treated with α,α-dibromo-m-xylene (6.6 g, 0.025 mol) in N,N-dimethylformamide (75 ml) at a temperature in the range of 20 to 25° C. and the reaction mixture stirred at this temperature for 16 hours. After removal of solvent, a viscous oil is obtained, which is treated with water (100 ml) and extracted with ethyl acetate (2×75 ml). The combined organic layers are washed with HCl (0.5 N, 75 ml), NaHCO$_3$ (5% b.w., 75 ml) and brine solution (75 ml). Removal of the solvent gives a crude solid that is triturated with toluene to give a white solid (4.84 g, 51%) of 4-hydroxybenzoic acid 1,3-phenylenebis(methylene)ester.

Example B

A mixture of 4-hydroxybenzoic acid (30.4 g, 0.22 mol), dichloro-o-xylene (15.4 g, 0.088 mol), potassium bicarbonate (24.2 g, 0.242 mol) and N,N-dimethylacetamide (27 g) are heated to 90° C. and held at this temperature for 4 hours. After cooling to 50° C., water (100 g) is added and the solution is allowed to cool to 25° C. After precipitation, the solids are filtered, washed with water (8×30 ml) and dried. This gives a white solid (31 g), which is a mixture of 4-hydroxy-benzoic acid 1,2-phenylenebis(methylene)ester and the corresponding compound (2) (ratio compound of type (1) to (2)=76:14 by HPLC).

Example C

A mixture of 4-hydroxybenzoic acid (6.9 g, 0.05 mol), dibromo-o-xylene (6.6 g, 0.025 mol), sodium carbonate (5.5 g) and N,N-dimethylformamide (100 ml) are stirred at 20° C. and held at this temperature for 24 hours. The reaction mixture is then poured onto water (400 g) and is stirred for 1 hour. After precipitation, the solids are filtered, washed with water (8×30 ml) and dried. This gives a white solid (31 g), which is a mixture of 4-hydroxybenzoic acid 1,2-phenylenebis(methylene)ester and the corresponding compound (2) (ratio compound of type (1) to (2)=80:16 by HPLC).

Example D

A mixture of 4-hydroxybenzoic acid (13.8 g, 0.1 mol), dibromo-m-xylene (10.9 g, 0.041 mol), sodium carbonate (10.6 g) and N,N-dimethylformamide (100 ml) are stirred at 20° C. and held at this temperature for 24 hours. The reaction mixture is then treated with water (100 g) and extracted with ethyl acetate (3×150 ml). The organic solvent was then removed under reduced pressure and the resulting oil treated with water (200 ml). After precipitation, the solids are filtered, washed with water (8×30 ml) and dried. This gives a white solid (13.5 g), which is a mixture of 4-hydroxy-benzoic acid 1,3-phenylenebis(methylene) ester and the corresponding compound (2) (ratio compound of type (1) to (2)=79:9 by HPLC).

Example E

A mixture of 4-hydroxybenzoic acid (9.13 g, 0.66 mol), dichloro-o-xylene (3.85 g, 0.022 mol), potassium bicarbonate (11.3 g) and N,N-dimethylacetamide (27 g) are heated to 90° C. and held at this temperature for 2.5 hours. After cooling to 60° C., water (100 g) is added and the solution is allowed to cool to 25° C. After precipitation, the solids are filtered, washed with water (8×30 ml) and dried. This gives a white solid (7.4 g), which is a mixture of 4-hydroxy-benzoic acid 1,2-phenylenebis(methylene)ester and the corresponding compound (2) (ratio compound of type (1) to (2)=82:15 by HPLC).

Example F

A mixture of 4-hydroxybenzoic acid (69.0 g, 0.5 mol), dibromo-o-xylene (66.0 g, 0.25 mol), sodium carbonate (11.3 g) and N,N-dimethylformamide (1 l) are stirred at 20° C. for 19 hours. The reaction mass was then poured onto 20% aqueous sodium bicarbonate solution (1.5 l) and the solid formed (97.6 g) was filtered. The solid was then extracted into acetonitrile (1 l), filtered and then the solvent was removed under reduced pressure. The oil obtained was treated with water (400 ml) and the precipitate was filtered, washed with water (3×50 ml) and dried. This gives a white solid (37.5 g), which is a mixture of 4-hydroxy-benzoic acid 1,2-phenylenebis(methylene)ester and the corresponding compound (2) (ratio compound of type (1) to (2)=72:14 by HPLC).

Example G

The N,N-dimethylformamide/20% aqueous sodium bicarbonate liquors from Example F above where extracted with ethyl acetate (2×500 ml). The combined organic extracts were washed with water (2×150 ml) and then evaporated under reduced pressure. This gave a white solid (32.5 g) which was purified using column chromatography to give 4-hydroxybenzoic acid 1,2-phenylenebis(methylene)ester as a white solid (99% purity).

Example H

A mixture of 4-hydroxybenzoic acid (45.7 g, 0.33 mol), dichloro-o-xylene (19.25 g, 0.11 mol), potassium bicarbonate (56.5 g, 0.56 mol) and N,N-dimethylacetamide (135 g) are heated to 90° C. and held at this temperature for 2 hours. After cooling to 50° C., water (550 g) is added and the solution is allowed to cool to 25° C. After precipitation, the solids are filtered, washed with water (2×75 ml) and dried. This gives a white solid (40.3 g), which is a mixture of 4-hydroxy-benzoic acid 1,2-phenylenebis(methylene)ester and the corresponding compound (2) (ratio compound of type (1) to (2)=88:12 by HPLC).

Example I

A mixture of 4-hydroxybenzoic acid (60.8 g, 0.440 mol) and N,N-dimethyl-acetamide (54 g) are heated to 50-55° C. and treated with potassium bicarbonate (48.4 g, 0.484 mol). Dichloro-o-xylene (30.8 g, 0.176 mol) is then added and the reaction mixture heated to 90° C. and held at this temperature for 4.5 hours. After cooling to 60° C., methanol (40 g) is added, followed by water (200 g) and the solution is allowed to cool to 25° C. After precipitation, the solids are filtered, washed with water (2×75 ml) and dried. This gives a white solid (62.0 g), which is a mixture of 4-hydroxy-benzoic acid 1,2-phenylenebis-(methylene)ester and the corresponding compound (2) (ratio compound of type (1) to (2)=79:15 by HPLC).

Example J

A mixture of 4-hydroxybenzoic acid (9.13 g, 0.022 mol) and N,N-dimethyl-acetamide (100 ml) at 25° C. is treated with potassium bicarbonate (11.3 g, 0.112 mol). Dibromo-o-xylene (30.8 g, 0.176 mol) is added and the reaction mixture is then held at 25° C. for 20 hours. The reaction mass is then poured onto water (400 ml) and the solids are filtered, washed with water (3×50 ml) and dried. This gives 4-hydroxy-benzoic acid 1,2-phenylenebis-(methylene)ester as a white solid (8.6 g, 98% purity, mp 210 to 213° C.).

Example K

A mixture of 4-hydroxybenzoic acid (152.0 g, 1.100 mol) and N,N-dimethyl-acetamide (135 g) are heated to 50 to 55° C. and treated with potassium bicarbonate (121.0 g, 1.210 mol). Dichloro-o-xylene (77.0 g, 0.44 mol) is then added and the reaction mixture heated to 90° C. and held at this temperature for 4.5 hours. After cooling to 60° C., methanol (100 g) is added, followed by water (500 g) and the solution is allowed to cool to 25° C. After precipitation, the solids are filtered, washed with water (3×250 ml) and dried. This gives a white solid (156.8 g), which is a mixture of 4-hydroxybenzoic acid 1,2-phenylenebis-(methylene)ester and the corresponding compound (2) (ratio compound of type (1) to (2)=80:13 by HPLC).

Example L

A mixture of 4-hydroxybenzoic acid (30.4 g, 0.220 mol) and dimethylsulfoxide (27 g) are heated to 50 to 55° C. and treated with potassium bicarbonate (24.2 g, 0.242 mol). Dichloro-o-xylene (15.4 g, 0.088 mol) is then added and the reaction mixture heated to 80° C. and held at this temperature for 2 hours. After cooling to 60° C., methanol (20 g) is added, followed by water (100 g) at 30° C. After precipitation, the solids are filtered, washed with water (4×50 ml) and dried. This gives a white solid (30.7 g), which is a mixture of 4-hydroxybenzoic acid 1,2-phenylenebis-(methylene)ester and the corresponding compound (2) (ratio compound of type (1) to (2)=74.8:12.1 by HPLC).

Example M

A mixture of 4-hydroxybenzoic acid (17.26 g, 0.125 mol), dichloro-o-xylene (8.75 g, 0.05 mol) and triethanolamine (18.64 g, 0.125 mol) are heated to 90° C. and held at this temperature for 1.5 hours. After cooling to 60° C., methanol (15 ml) is added, followed by water (100 g) and the solution is allowed to cool to 25° C. After precipitation, the solids are filtered, washed with water (3×50 ml) and dried. This gives a white solid (15.2 g), which is a mixture of 4-hydroxy-benzoic acid 1,2-phenylenebis-methylene)ester and the corresponding compound (2) (ratio compound of type (1) to (2)=82:13 by HPLC).

Example N

A mixture of 4-hydroxybenzoic acid (30.4 g, 0.220 mol) and PEG-200 (30 g) are heated to 50 to 55° C. and treated with potassium bicarbonate (24.2 g, 0.242 mol). Dichloro-o-xylene (15.4 g, 0.088 mol) is then added and the reaction mixture heated to 90° C. and held at this temperature for 2 hours. After cooling to 60° C., methanol (10 g) is added, followed by water (100 g) at 30° C. After precipitation, the solids are filtered, washed with water (4×50 ml) and dried. This gives a white solid (29.6 g), which is a mixture of 4-hydroxy-benzoic acid 1,2-phenylenebis-(methylene)ester and the corresponding compound (2) (ratio compound of type (1) to (2)=64:20 by HPLC).

Example O

A mixture of 4-hydroxybenzoic acid (73.0 g, 0.528 mol) and N,N-dimethyl-acetamide (64.8 g) are heated to 50 to 55° C. and treated with potassium carbonate (40.1 g, 0.290 mol). Dichloro-o-xylene (37.0 g, 0.21 mol) is then added and the reaction mixture heated to 90° C. and held at this temperature for 5 hours. N,N-dimethylacetamide (64.8 g) is then added and the suspension is filtered, the solid is washed with hot N,N-dimethylacetamide (50.0 g). The combined mother liquors and wash are distilled under vacuum to remove N,N-dimethylacetamide (147 g). Water (200 g) is added to the viscous mass, the mixture is allowed to cool to 30° C. The precipitated solids are filtered, washed with water (5×200 g) and dried. This gives a white solid (71.7 g), which is a mixture of 4-hydroxy-benzoic acid 1,2-phenylenebis-(methylene)ester and the corresponding compound (2) (ratio compound of type (1) to (2)=80:13 by HPLC).

Example P

A mixture of 4-hydroxybenzoic acid (73.0 g, 0.528 mol) and N,N-dimethyl-acetamide (64.8 g) are heated to 50 to 55° C. and treated with potassium carbonate (40.1 g, 0.290 mol). Dichloro-o-xylene (37.0 g, 0.21 mol) is then added and the reaction mixture heated to 90° C. and held at this temperature for 5 hours. N,N-dimethyl-acetamide (64.8 g) is then added and the suspension is filtered, the solid is washed with N,N-dimethylacetamide (50.0 g). The combined mother liquors and wash are distilled under vacuum to remove N,N-dimethylacetamide (113 g). After cooling to 60° C., methanol (52.8 g) is added, followed by water (240 g) and the solution is allowed to cool to 25° C. After precipitation, the solids are filtered, washed with water (5×200 ml) and dried. This gives a white solid (70.9 g), which is a mixture of 4-hydroxybenzoic acid 1,2-phenylenebis-methylene)ester and the corresponding compound (2) (ratio compound of type (1) to (2)=80:13 by HPLC).

APPLICATION EXAMPLES 1-10

The following examples illustrate the invention in further detail but are not limitative of the scope of the invention. In the examples, unless otherwise stated, parts and % are parts by weight and % by weight, respectively.

Example 1

Preparation of Dispersion A-1

| | |
|---|---|
| 3-dibutyamino-6-methyl-7-anilinofluoran | 6 parts |
| 10% aqueous solution of polyvinyl alcohol | 30 parts |
| water | 4 parts |

The mixture of the above components is pulverised in a bead mill to a mean particle size of 1.0 μm.

Preparation of Dispersion B-1

| | |
|---|---|
| colour developer of Example C | 12 parts |
| 10% aqueous solution of polyvinyl alcohol (PVA-203 manufactured by Kuraray Co. Ltd) | 12 parts |
| 45% aqueous solution of sodium naphthalene sulphonate polymer with formaldehyde | 0.6 parts |
| water | 35.4 parts |

The mixture of the above components is pulverised in a bead mill to a mean particle size of 1.0 μm.

Preparation of Dispersion C-1

| | |
|---|---|
| 2-naphthyl benzyl ether | 12 parts |
| 10% aqueous solution of polyvinyl alcohol (PVA-203 manufactured by Kuraray Co. Ltd) | 12 parts |
| water | 36 parts |

The mixture of the above components is pulverised in a bead mill to a mean particle size of 1.0 μm.

Preparation of Dispersion D-1

| | |
|---|---|
| precipitated calcium carbonate (Socal® P3 manufactured by Solvay Chemicals) | 55.5 parts |
| sodium polyacrylate dispersant | 0.5 parts |
| water | 36.5 parts |

The mixture of the above components is pulverised in a bead mill to a mean particle size of 1.0 μm.

40 parts of Dispersion A-1, 60 parts of Dispersion B-1, 60 parts of Dispersion C-1, 92.5 parts of Dispersion D-1, 29.5 parts of a 17% zinc stearate dispersion (Hidorin F 115, Chukyo Europe), 18 parts of 20% aqueous polyvinyl alcohol solution and 0.5 parts of Ciba® Tinopal® ABP-X fluorescent whitening agent are mixed with stirring.

The coating composition thus obtained is applied to a base paper (having a pre-coating comprising organic hollow spheres having an average particle diameter of 1.0 μm; shell material: styrene/acrylic copolymer; weighing 50 g/m$^2$ in an amount of 6 g/m$^2$ (on a dry basis), followed by drying and calendering to 400 Bekk seconds smoothness to give a heat sensitive recording paper.

Example 2

A coating composition is prepared as in Example 1 with the exception that 60 parts of Dispersion C-1 are replaced with 60 parts of a 20% dispersion of stearamide (Hymicron G-270, Chukyo Europe) and 18 parts of aqueous PVA 203 polyvinyl alcohol solution are replaced with 24 parts of aqueous polyvinyl alcohol solution.

Example 3

A coating composition is prepared as in Example 1 with the exception that in the preparation of Dispersion B-1, 12 parts of colour developer of Example C are replaced with 12 parts of colour developer of Example D.

Example 4

A coating composition is prepared as in Example 3 with the exception that 60 parts of Dispersion C-1 are replaced with 60 parts of a 20% dispersion of stearamide (Hymicron G-270, Chukyo Europe) and 18 parts of aqueous polyvinyl alcohol solution are replaced with 24 parts of aqueous polyvinyl alcohol solution.

Example 5

A coating composition is prepared as in Example 1 with the exception that in the preparation of Dispersion A-1, 6 parts of 3-dibutylamino-6-methyl-7-anilinofluoran are replaced with 6 parts of 3-(N-ethyl, N-isopentylamino)-6-methyl-7-aminofluoran.

Example 6

A coating composition is prepared as in Example 5 with the exception that in the preparation of Dispersion B-1, 12 parts of colour developer of Example C are replaced with 12 parts of colour developer of Example D.

Example 7

A coating composition is prepared as in Example 1 with the exception that in the preparation of Dispersion A-1, 6 parts of 3-dibutylamino-6-methyl-7-anilinofluoran are replaced with 6 parts of 3-diethylamino-6-methyl-7-anilinofluoran.

Example 8

A coating composition is prepared as in Example 7 with the exception that in the preparation of Dispersion B-1, 12 parts of colour developer of Example C are replaced with 12 parts of colour developer of Example D.

Example 9

A coating composition is prepared as in Example 2 with the exception that in the preparation of Dispersion B-1, 12 parts of colour developer of Example C are replaced with 12 parts of colour developer of Example E.

Example 10

A coating composition is prepared as in Example 1 with the exception that in the preparation of Dispersion A-1, 6 parts of 3-dibutylamino-6-methyl-7-anilinofluoran are replaced with 6 parts of 3-(N-ethyl-N-p-tolylamino)-6-methyl-7-anilinofluoran; in the preparation of Dispersion B-1, 12 parts of colour developer of Example C are replaced with 12 parts of colour developer of Example H and in the preparation of Dispersion C-1, 12 parts of 2-naphthyl benzyl ether are replaced with 12 parts of 1,2-di(3-methylphenoxy)ethane.

Examples 11-29

Preparation of Dispersion A-2

| | |
|---|---|
| 3-dibutylamino-6-methyl-7-anilinofluoran | 10 parts |
| 10% aqueous solution of polyvinyl alcohol (PVA-203 manufactured by Kuraray Co. Ltd) | 15 parts |
| water | 15 parts |

The mixture of the above components is pulverised in a bead mill to a mean particle size of 1.0 μm.

Preparation of Dispersion B-2

| | |
|---|---|
| colour developer of Example H | 20 parts |
| 10% aqueous solution of polyvinyl alcohol (PVA-203 manufactured by Kuraray Co. Ltd) | 30 parts |
| 45% aqueous solution of sodium naphthalene sulphonate polymer with formaldehyde | 1 part |
| water | 29 parts |

The mixture of the above components is pulverised in a bead mill to a mean particle size of 1.0 μm.

Preparation of Dispersion C-2

| | |
|---|---|
| 1,2-di(3-methylphenoxy)ethane | 20 parts |
| 10% aqueous solution of polyvinyl alcohol (PVA-203 manufactured by Kuraray Co. Ltd) | 30 parts |
| Water | 30 parts |

The mixture of the above components is pulverised in a bead mill to a mean particle size of 1.0 μm.

Preparation of Dispersion D-2

| | |
|---|---|
| precipitated calcium carbonate (Socal ® P3 manufactured by Solvay Chemicals) | 30 parts |
| sodium polyacrylate dispersant | 0.1 parts |
| water | 69.9 parts |

The mixture of the above components is pulverised in a bead mill to a mean particle size of 1.0 μm.

Preparation of Dispersion D-3

| | |
|---|---|
| aluminium trihydroxide (Martifin ® OL-107 manufactured by Martinswerk GmbH) | 30 parts |
| sodium polyacrylate dispersant | 0.1 parts |
| water | 69.9 parts |

The mixture of the above components is pulverised in a bead mill to a mean particle size of 1.0 μm.

Preparation of Dispersion D-4

| | |
|---|---|
| amorphous silica (Thermosil manufactured by Süd Chemie AG) | 30 parts |
| sodium polyacrylate dispersant | 0.13 parts |
| Water | 69.87 parts |

The mixture of the above components is pulverised in a bead mill to a mean particle size of 1.0 μm.

Preparation of Dispersion D-5

| | |
|---|---|
| china clay (China Clay SPS manufactured by ECC International) | 30 parts |
| sodium polyacrylate dispersant | 0.1 parts |
| water | 69.9 parts |

The mixture of the above components is pulverised in a bead mill to a mean particle size of 1.0 μm.

Example 11

40 parts of Dispersion A-2, 80 parts of Dispersion B-2, 80 parts of Dispersion C-2, 100 parts of Dispersion D-2, 38.25 parts of a 17% zinc stearate dispersion (Hidorin F 115, Chukyo Europe), 27.5 parts of 20% aqueous PVA 203 polyvinyl alcohol solution and 0.5 parts of Ciba® Tinopal® ABP-X fluorescent whitening agent are mixed with stirring.

The coating composition thus obtained is applied to a base paper [having a pre-coating comprising Ansilex® 93 clay (Engelhard Corporation)] weighing 50 g/m² in an amount of 5 g/m² (on a dry basis), followed by drying and calendering to 400 Bekk seconds smoothness to give a heat sensitive recording paper.

Example 12

A coating composition is prepared as in Example 11 with the exception that 100 parts of Dispersion D-2 are replaced with 100 parts of Dispersion D-3.

Example 13

A coating composition is prepared as in Example 11 with the exception that 100 parts of Dispersion D-2 are replaced with 100 parts of Dispersion D-4.

Example 14

A coating composition is prepared as in Example 11 with the exception that 100 parts of Dispersion D-2 are replaced with 100 parts of Dispersion D-5.

Example 15

A coating composition is prepared as in Example 11 with the exception that 100 parts of Dispersion D-2 are replaced with 48.8 parts of a 61.5% aqueous dispersion of talc (Finntalc C10 XR manufactured by Mondo Minerals Oy) and 51.2 parts of water.

Example 16

A coating composition is prepared as in Example 2 with the exception that in the preparation of Dispersion B-1, 12 parts of color developer of Example C are replaced with 12 parts of colour developer of Example J.

Example 17

A coating composition is prepared as in Example 11 with the exception that in the preparation of Dispersion B-2, 20 parts of colour developer of Example H are replaced with 20 parts of colour developer of Example K and in the preparation of dispersion C-2, 20 parts of 1,2-di(3-methylphenoxy)ethane are replaced with 20 parts of 2-naphthyl benzyl ether.

Example 18

A coating composition is prepared as in Example 11 with the exception that in the preparation of Dispersion B-2, 20 parts of colour developer of Example H are replaced with 20 parts of colour developer of Example K and in the preparation of Dispersion C-2, 20 parts of 1,2-di(3-methylphenoxy)ethane are replaced with 20 parts of 1,2-diphenoxyethane.

Example 19

A coating composition is prepared as in Example 18 with the exception that in the preparation of Dispersion A-2, 10 parts of 3-dibutylamino-6-methyl-7-anilinofluoran are replaced with 10 parts of 3-dipentylamino-6-methyl-7-anilinofluoran.

Example 20

A coating composition is prepared as in Example 11 with the exception that in the preparation of Dispersion B-2, 20 parts of colour developer of Example H are replaced with 20 parts of colour developer of Example K and in the preparation of Dispersion C-2, 20 parts of 1,2-di(3-methylphenoxy)ethane are replaced with 20 parts of di(p-methylbenzyl)oxalate.

Example 21

A coating composition is prepared as in Example 20 with the exception that in the preparation of Dispersion A-2, 10 parts of 3-dibutylamino-6-methyl-7-anilinofluoran are replaced with 10 parts of 3-dipentylamino-6-methyl-7-anilinofluoran.

Example 22

A coating composition is prepared as in Example 11 with the exception that in the preparation of Dispersion B-2, 20 parts of colour developer of Example H are replaced with 20 parts of colour developer of Example K and in the preparation of Dispersion C-2, 20 parts of 1,2-di(3-methylphenoxy)ethane are replaced with 20 parts of 1,2-bis(3,4-dimethylphenyl)ethane.

Example 23

A coating composition is prepared as in Example 11 with the exception that in the preparation of Dispersion B-2, 20 parts of colour developer of Example H are replaced with a mixture of 20 parts of colour developer of Example K and 5 parts of 1,1,3-tris(3'-cyclohexyl-4'-hydroxy-6'-methylphenyl)butane and in the preparation of Dispersion D-2, 30 parts of precipitated calcium carbonate are replaced with 25 parts of precipitated calcium carbonate.

Example 24

A coating composition is prepared as in Example 11 with the exception that in the preparation of of Dispersion B-2, 20 parts of colour developer of Example H are replaced with a mixture of 20 parts of colour developer of Example K and 5 parts of 1,1,3-bis(3'-tert-butyl-4'-hydroxy-6'-methylphenyl)butane and in the preparation of Dispersion D-2, 30 parts of precipitated calcium carbonate are repalced with 25 parts of precipitated calcium carbonate.

Example 25

A coating composition is prepared as in Example 11 with the exception that in the preparation of of Dispersion A-2, 10 parts of 3-dibutylamino-6-methyl-7-anilinofluoran are replaced with a mixture of 7 parts of 3-dibutylamino-6-methyl-7-anilinofluoran and 3 parts of 3-(N-ethyl,N-isopentylamino)-6-methyl-7-anilinofluoran; in the preparation of Dispersion B-2, 20 parts of colour developer of Example H are replaced with 20 parts of colour developer of Example K and in the preparation of Dispersion C-2, 20 parts of 1,2-di(3-methylphenoxy)ethane are replaced with 20 parts of p-tolyl biphenyl ether.

Example 26

A coating composition is prepared as in Example 11 with the exception that in the preparation of of Dispersion A-2, 10 parts of 3-dibutylamino-6-methyl-7-anilinofluoran are replaced with 10 parts of 3,3-bis(4-dimethylaminophenyl)-6-dimethylaminophthalide; in the preparation of Dispersion B-2, 20 parts of colour developer of Example H are replaced with 20 parts of colour developer of Example K; 80 parts of Dispersion C-2 are replaced with 100 parts of a 20% dispersion of stearamide (Hymicron G-270, Chukyo Europe) and 27.5 parts of aqueous polyvinyl alcohol solution are replaced with 42.5 parts of aqueous PVA 203 polyvinyl alcohol solution.

Example 27

A coating composition is prepared as in Example 11 with the exception that in the preparation of of Dispersion A-2, 10 parts of 3-dibutylamino-6-methyl-7-anilinofluoran are replaced with 10 parts of 3-diethylaminofluoran-7-carboxylic acid, ethyl ester and in the preparation of Dispersion B-2, 20 parts of colour developer of Example H are replaced with 20 parts of colour developer of Example K.

Example 28

A coating composition is prepared as in Example 11 with the exception that in the preparation of of Dispersion A-2, 10 parts of 3-dibutylamino-6-methyl-7-anilinofluoran are replaced with 10 parts of 3-diethylamino-benzo[a]fluoran and in the preparation of Dispersion B-2, 20 parts of colour developer of Example H are replaced with 20 parts of colour developer of Example K.

Example 29

A coating composition is prepared as in Example 11 with the exception that in the preparation of of Dispersion A-2, 10 parts of 3-dibutylamino-methyl-7-anilinofluoran are replaced with 10 parts of 3-diethylamino-6,8-dimethylfluoran and in the preparation of Dispersion B2, 20 parts of colour developer of Example H are replaced with 20 parts of colour developer of Example K.

Example 30

A coating composition is prepared as in Example 11 with the exception that in the preparation of Dispersion B-2, 20 parts of colour developer of Example H are replaced with 20 parts of colour developer of Example K. The coating composition is applied to a base paper weighing 50 g/m$^2$ in an amount of 5.5 g/m$^2$ (on a dry basis), followed by drying and calendering to 400 Bekk seconds smoothness to give a heat sensitive recording paper. The base paper had been pre-coated with a mixture of Ansilex® clay (Engelhard Corporation) and Ropaque® (Rohm & Haas) styrene/acrylic hollow spheres.

Example 31

A coating composition is prepared as in Example 30 with the exception that in the preparation of dispersion C-2, 20 parts of 1,2-di(3-methylphenoxy)ethane are replaced with 20 parts of 2-naphthyl benzyl ether.

Example 32

A coating composition is prepared as in Example 30 with the exception that in the preparation of dispersion A-2, 10 parts of 3-dibutylamino-6-methyl-7-anilinofluoran are replaced with 10 parts of 3-diethylamino-6-methyl-7(3-methylphenylamino)fluoran.

Example 33

A coating composition is prepared as in Example 32 with the exception that in the preparation of dispersion C-2, 20 parts of 1,2-di(3-methylphenoxy)ethane are replaced with 20 parts of 2-naphthyl benzyl ether.

Example 34

A coating composition is prepared as in Example 30 with the exception that in the preparation of dispersion A-2, 10 parts of 3-dibutylamino-6-methyl-7-anilinofluoran are replaced with 10 parts of 3-(N-methyl, N-cyclohexylamino)-6-methyl-7-anilinofluoran. The coating was applied to the pre-coated base paper with a coatweight of about 5 g/m$^2$.

Example 35

A coating composition is prepared as in Example 31 with the exception that in the preparation of dispersion A-2, 10 parts of 3-dibutylamino-methyl-7-anilinofluoran are replaced with 10 parts of 3-(N-ethyl, N-isopentylamino-6-methyl-7-anilinofluoran. The coating was applied to the pre-coated base paper with a coatweight of about 5 g/m$^2$.

Example 36

A coating composition is prepared as in Example 30 with the exception that in the preparation of dispersion A-2, 10 parts of 3-dibutylamino-6-methyl-7-anilinofluoran are replaced with 10 parts of 3-(4-diethylamino-2-ethoxyphenyl)-3-(1-octyl-2-methylindole-3-yl)-4-azaphthalide and 80 parts of Dispersion C-2 are replaced with 100 parts of a 20% aqueous dispersion of stearamide (Hymicron G-270, Chukyo Europe). The coating was applied to the pre-coated base paper with a coatweight of about 5 g/m$^2$.

Example 37

A coating composition is prepared as in Example 35 with the exception that 80 parts of Dispersion C-2 are replaced with 100 parts of a 20% aqueous dispersion of stearamide (Hymicron G-270, Chukyo Europe). The coating was applied to the pre-coated base paper with a coatweight of about 5 g/m$^2$.

Example 38

40 Parts of Dispersion A-2, 80 parts of Dispersion B-2 in which the colour developer of Example H is replaced by the colour developer of Example K, 150 parts of Dispersion C-1. 33.3 parts of Dispersion D-2, 38.25 parts of a 17% zinc stearate dispersion (Hidorin F 115, Chukyo Europe), 27.5 parts of 20% aqueous PVA 203 polyvinyl alcohol solution and 0.5 parts of Ciba® Tinopal® ABP-X fluorescent whitening agent are mixed with stirring.

The coating composition thus obtained is applied to a base paper [having a pre-coating comprising Ansilex® 93 clay (Engelhard Corporation)] weighing 50 g/m$^2$ in an amount of g/m$^2$ (on a dry basis), followed by drying and calendering to 400 Bekk seconds smoothness to give a heat sensitive recording paper.

A protective layer comprising Coating Composition E-1 was then applied in an amount of 3 g/m$^2$ (on a dry basis) to the heat sensitive recording material, followed by drying and calendering to 400 Bekk seconds smoothness.

Preparation of Coating Composition E-1

| | |
|---|---|
| 10% aqueous solution of polyvinyl alcohol (PVA-105 manufactured by Kuraray Co. Ltd) | 100 parts |
| Ansilex 93 calcined clay (Engelhard Corporation) | 10 parts |
| 17% zinc stearate dispersion (Hidorin F 115, Chukyo Europe) | 5.9 parts |
| 40% aqueous solution of glyoxal | 2.5 parts |
| Water | 39 parts |

Example 39

A heat sensitive recording paper containing a protective layer was prepared as in Example 38 with the exception that Coating Composition E-1 was replaced by Coating Composition E-2.

Preparation of Coating Composition E-2

| | |
|---|---|
| 10% aqueous solution of carboxylated polyvinyl alcohol (Poval KM 618K manufactured by Kuraray Co. Ltd) | 80 parts |
| aluminium trihydroxide (Martifin ® OL-107 manufactured by Martinswerk GmbH) | 10 parts |
| sodium polyacrylate dispersant | 0.25 parts |
| 17% zinc stearate dispersion (Hidorin F 115, Chukyo Europe) | 5.9 parts |
| 40% aqueous solution of glyoxal | 2.5 parts |
| Water | 40 parts |

Example 40

A heat sensitive recording paper containing a protective layer was prepared as in Example 38 with the exception that Coating Composition E-1 was replaced by Coating Composition E-3.

Preparation of Coating Composition E-3

| | |
|---|---|
| 10% aqueous solution of acetoacetyl-modified polyvinyl alcohol (Gohsefimer Z-200 manufactured by Nippon Synthetic Chemical Industry) | 50 parts |
| Kaolin (Astra Plate SD manufactured by Imerys) | 15 parts |
| 17% zinc stearate dispersion (Hidorin F 115, Chukyo Europe) | 6.6 parts |
| Water | 85 parts |

Example 41

A heat sensitive recording paper containing a protective layer was prepared as in Example 38 with the exception that Coating Composition E-1 was replaced by Coating Composition E-4.

Preparation of Coating Composition E-4

| | |
|---|---|
| 10% aqueous solution of silanol-modified polyvinyl alcohol (PVA R-3109 manufactured by Kuraray Co. Ltd.) | 70 parts |
| aluminium trihydroxide (Martifin ® OL-107 manufactured by Martinswerk GmbH) | 2.7 parts |
| 17% zinc stearate dispersion (Hidorin F 115, Chukyo Europe) | 1.8 parts |

Example 42

A heat sensitive recording paper containing a protective layer was prepared as in Example 38 with the exception that Coating Composition E-1 was replaced by Coating Composition E-5 and the paper was calendered to 1000 Bekk seconds smoothness.

Preparation of Coating Composition E-5

| | |
|---|---|
| 10% aqueous solution of silanol-modified polyvinyl alcohol (PVA R-3109 manufactured by Kuraray Co. Ltd.) | 70 parts |
| aluminium trihydroxide (Martifin ® OL-107 manufactured by Martinswerk GmbH) | 2.4 parts |
| 17% zinc stearate dispersion (Hidorin F 115, Chukyo Europe) | 1.8 parts |
| 40% aqueous solution of glyoxal | 0.8 parts |

Example 43

A heat sensitive recording paper containing a protective layer was prepared as in Example 38 with the exception that Coating Composition E-1 was replaced by Coating Composition E-6 and the paper was calendered to 1000 Bekk seconds smoothness.

Preparation of Coating Composition E-6

| | |
|---|---|
| 10% aqueous solution of carboxylated polyvinyl alcohol (Poval KM 618K manufactured by Kuraray Co. Ltd) | 100 parts |
| Kaolin (Astra Plate SD manufactured by Imerys) | 20 parts |
| 17% zinc stearate dispersion (Hidorin F 115, manufactured by Chukyo Europe) | 8.8 parts |
| 13% aqueous solution of polyamide-epichlorohydrin resin (Polycup ® LX resin, manufactured by Hercules Ltd.) | 30.8 parts |
| water | 190 parts |

Example 44

A heat sensitive recording paper containing a protective layer was prepared as in Example 38 with the exception that Coating Composition E-1 was replaced by Coating Composition E-7 and the paper was calendered to 1000 Bekk seconds smoothness.

Preparation of Coating Composition E-7

| | |
|---|---|
| 10% aqueous solution of carboxylated polyvinyl alcohol (Poval KM 618K manufactured by Kuraray Co. Ltd) | 100 parts |
| aluminium trihydroxide (Martifin ® OL-107 manufactured by Martinswerk GmbH) | 20 parts |
| 17% zinc stearate dispersion (Hidorin F 115, manufactured by Chukyo Europe) | 8.8 parts |

-continued

| | |
|---|---|
| 13% aqueous solution of polyamide-epichlorohydrin resin (Polycup ® LX resin, manufactured by Hercules Ltd.) | 30.8 parts |
| water | 131 parts |

Example 45

A heat sensitive recording paper containing a protective layer was prepared as in Example 38 with the exception that Coating Composition E-1 was replaced by Coating Composition E-8.

Preparation of Coating Composition E-8

| | |
|---|---|
| 10% aqueous solution of silanol-modified polyvinyl alcohol (PVA R-3109 manufactured by Kuraray Co. Ltd.) | 157.5 parts |
| aluminium trihydroxide (Martifin ® OL-107 manufactured by Martinswerk GmbH) | 80 parts |
| 17% zinc stearate dispersion (Hidorin F 115, Chukyo Europe) | 11.7 parts |
| 40% aqueous solution of glyoxal | 5.6 parts |
| water | 250 parts |

Example 46

A heat sensitive recording paper containing a protective layer was prepared as in Example 38 with the exception that Coating Composition E-1 was replaced by Coating Composition E-9.

Preparation of Coating Composition E-9

| | |
|---|---|
| 10% aqueous solution of silanol-modified polyvinyl alcohol (PVA R-3109 manufactured by Kuraray Co. Ltd.) | 157.5 parts |
| aluminium trihydroxide (Martifin ® OL-107 manufactured by Martinswerk GmbH) | 80 parts |
| 17% zinc stearate dispersion (Hidorin F 115, manufactured by Chukyo Europe) | 11.7 parts |
| 13% aqueous solution of polyamide-epichlorohydrin resin (Polycup ® LX resin, manufactured by Hercules Ltd.) | 17.3 parts |
| water | 250 parts |

Examples 47-49

Preparation of Dispersion A-3

| | |
|---|---|
| 3-dibutylamino-6-methyl-7-anilinofluoran | 10 parts |
| 10% aqueous solution of polyvinyl alcohol (PVA-203 manufactured by Kuraray Co. Ltd) | 20 parts |
| water | 10 parts |

The mixture of the above components is pulverised in a bead mill to a mean particle size of 1.0 μm.

Preparation of Dispersion B-3

| | |
|---|---|
| colour developer of Example K | 25 parts |
| 10% aqueous solution of polyvinyl alcohol (PVA-203 manufactured by Kuraray Co. Ltd) | 5 parts |
| 45% aqueous solution of sodium naphthalene sulphonate polymer with formaldehyde | 1.1 parts |
| water | 40.4 parts |

The mixture of the above components is pulverised in a bead mill to a mean particle size of 1.0 μm.

Preparation of Dispersion C-3

| | |
|---|---|
| 1,2-di(3-methylphenoxy)ethane | 20 parts |
| 10% aqueous solution of polyvinyl alcohol (PVA-203 manufactured by Kuraray Co. Ltd) | 6.7 parts |
| 45% aqueous solution of sodium naphthalene sulphonate polymer with formaldehyde | 0.8 parts |
| Water | 52.5 parts |

The mixture of the above components is pulverised in a bead mill to a mean particle size of 1.0 μm.

Preparation of Dispersion D-6

| | |
|---|---|
| precipitated calcium carbonate (Socal ® P3 manufactured by Solvay Chemicals) | 25 parts |
| sodium polyacrylate dispersant | 0.25 parts |
| water | 16.4 parts |

The mixture of the above components is pulverised in a bead mill to a mean particle size of 1.0 μm.

Example 47

40 parts of Dispersion A-3, 71.5 parts of Dispersion B-3, 80 parts of Dispersion C-3, 41.65 parts of Dispersion D-6, 38.25 parts of a 17% zinc stearate dispersion (Hidorin F 115, Chukyo Europe), 49.2 parts of 20% aqueous PVA 203 polyvinyl alcohol solution and 2.2 parts of Ciba® Tinopal® ABP-Z fluorescent whitening agent are mixed with stirring.

The coating composition thus obtained is applied to a base paper [having a pre-coating comprising Ansilex® 93 day (Engelhard Corporation)] weighing 50 g/m² in an amount of 4.5 g/m² (on a dry basis), followed by drying and calendering to 400 Bekk seconds smoothness to give a heat sensitive recording paper.

Example 48

A coating composition is prepared as in Example 47 with the exception that in the preparation of Dispersion C-3, 20 parts of 1,2-di(3-methylphenoxy)ethane are replaced by 20 parts p-benzylbiphenyl.

Example 49

A coating composition is prepared as in Example 47 with the exception that in the preparation of Dispersion C-3, 20 parts of 1,2-di(3-methylphenoxy)ethane are replaced by 20 parts 2-naphthyl benzyl ether.

Preparation of Dispersion B-4

| | |
|---|---|
| colour developer of Example K | 20 parts |
| 10% aqueous solution of sulfonated polyvinyl alcohol (Gohseran L3266 manufactured by Nippon Gohsei) | 4.0 parts |
| 45% aqueous solution of sodium naphthalene sulphonate polymer with formaldehyde | 0.85 parts |
| water | 25.15 parts |

The mixture of the above components is pulverised in a bead mill to a mean particle size of 1.0 µm.

Preparation of Dispersion D-7

| | |
|---|---|
| precipitated calcium carbonate (Socal ® P3 manufactured by Solvay Chemicals) | 30 parts |
| sodium polyacrylate dispersant | 0.30 parts |
| water | 19.7 parts |

The mixture of the above components is pulverised in a bead mill to a mean particle size of 1.0 µm.

Example 50

40 parts of Dispersion A-3, 50 parts of Dispersion B-4, 80 parts of Dispersion C-3, 50 parts of Dispersion D-7, 38.25 parts of a 17% zinc stearate dispersion (Hidorin F 115, Chukyo Europe), 49.65 parts of 20% aqueous PVA 203 polyvinyl alcohol solution and 2.2 parts of Ciba® Tinopal® ABP-Z fluorescent whitening agent are mixed with stirring.

The coating composition thus obtained is applied to a base paper [having a pre-coating comprising Ansilex® 93 day (Engelhard Corporation)] weighing 50 g/m² in an amount of 4.5 g/m² (on a dry basis), followed by drying and calendering to 400 Bekk seconds smoothness to give a heat sensitive recording paper.

Example 51

A coating composition is prepared as in Example 50 with the exception that in the preparation of Dispersion C-3, 20 parts of 1,2-di(3-methylphenoxy)ethane are replaced by 20 parts p-benzylbiphenyl.

Example 52

A coating composition is prepared as in Example 50 with the exception that in the preparation of Dispersion C-3, 20 parts of 1,2-di(3-methylphenoxy)ethane are replaced by 20 parts 2-naphthyl benzyl ether.

Example 53

A coating composition is prepared as in Example 47 with the exception that in the preparation of Dispersion A-3, 10 parts of 3-dibutylamino-6-methyl-7-anilinofluoran are replaced by a mixture of 7.5 parts 3-dibutylamino-6-methyl-7-anilinofluoran and 2.5 parts 3-(N-ethyl, N-isopentylamino)-6-methyl-7-anilinofluoran.

Example 54

A coating composition is prepared as in Example 48 with the exception that in the preparation of Dispersion A-3, 10 parts of 3-dibutylamino-6-methyl-7-anilinofluoran are replaced by a mixture of 7.5 parts 3-dibutylamino-methyl-7-anilinofluoran and 2.5 parts 3-(N-ethyl, N-isopentylamino)-6-methyl-7-anilinofluoran.

Example 55

A coating composition is prepared as in Example 49 with the exception that in the preparation of Dispersion A-3, 10 parts of 3-dibutylamino-6-methyl-7-anilinofluoran are replaced by a mixture of 7.5 parts 3-dibutylamino-6-methyl-7-anilinofluoran and 2.5 parts 3-(N-ethyl, N-isopentylamino)-6-methyl-7-anilinofluoran.

Example 56

A coating composition is prepared as in Example 47 with the exception that in the preparation of Dispersion A-3, 10 parts of 3-dibutylamino-6-methyl-7-anilinofluoran are replaced by a mixture of 5 parts 3-dibutylamino-6-methyl-7-anilinofluoran and 5 parts 3-(N-ethyl, N-isopentylamino)-6-methyl-7-anilinofluoran.

Example 57

A coating composition is prepared as in Example 48 with the exception that in the preparation of Dispersion A-3, 10 parts of 3-dibutylamino-6-ethyl-7-anilinofluoran are replaced by a mixture of 5 parts 3-dibutylamino-6-methyl-7-anilinofluoran and 5 parts 3-(N-ethyl, N-isopentylamino)-6-methyl-7-anilinofluoran.

Example 58

A coating composition is prepared as in Example 49 with the exception that in the preparation of Dispersion A-3, 10 parts of 3-dibutylamino-6-methyl-7-anilinofluoran are replaced by a mixture of 5 parts 3-dibutylamino-6-methyl-7-anilinofluoran and 5 parts 3-N-ethyl, N-isopentylamino)-6-methyl-7-anilinofluoran.

Examples 59-61

Preparation of Dispersion B-5

| | |
|---|---|
| colour developer of Example K | 20 parts |
| 1,2-di(3-methylphenoxy)ethane | 20 parts |
| 10% aqueous solution of polyvinyl alcohol (PVA 203 manufatured by Kuraray Co. Ltd.) | 4.0 parts |
| 45% aqueous solution of sodium naphthalene sulphonate polymer with formaldehyde | 0.85 parts |
| water | 55.15 parts |

The mixture of the above components is pulverised in a bead mill to a mean particle size of 1.0 µm.

Example 59

40 parts of Dispersion A-3, 100 parts of Dispersion B-5, 50 parts of Dispersion D-7, 38.25 parts of a 17% zinc stearate dispersion (Hidorin F 115, Chukyo Europe), 53.0 parts of 20% aqueous PVA 203 polyvinyl alcohol solution and 2.2 parts of Ciba® Tinopal® ABP-Z fluorescent whitening agent are mixed with stirring.

The coating composition thus obtained is applied to a base paper [having a pre-coating comprising Ansflex® 93 clay (Engelhard Corporation)] weighing 50 g/m² in an amount of 4.5 g/m² (on a dry basis), followed by drying and calendering to 400 Bekk seconds smoothness to give a heat sensitive recording paper.

Example 60

A coating composition is prepared as in Example 59 with the exception that in the preparation of Dispersion B-5, 20 parts of 1,2-di(3-methylphenoxy)ethane are replaced with 20 parts p-benzylbiphenyl.

Example 61

A coating composition is prepared as in Example 59 with the exception that in the preparation of Dispersion B-5, 20 parts of 1,2-di(3-methylphenoxy)ethane are replaced with 20 parts 2-benzyl naphthyl ether.

Examples 62-64

Preparation of Dispersion B-6

| | |
|---|---|
| colour developer of Example K | 20 parts |
| 1,2-di(3-methylphenoxy)ethane | 20 parts |
| 10% aqueous solution of sulfonated polyvinyl alcohol (Gohseran L3266 manufactured by Nippon Gohsei) | 4.0 parts |
| 45% aqueous solution of sodium naphthalene sulphonate polymer with formaldehyde | 0.85 parts |
| water | 55.15 parts |

The mixture of the above components is pulverised in a bead mill to a mean particle size of 1.0 μm.

Example 62

40 parts of Dispersion A-3, 100 parts of Dispersion B-6, 50 parts of Dispersion D-7, 38.25 parts of a 17% zinc stearate dispersion (Hidorin F 115, Chukyo Europe), 53.0 parts of 20% aqueous PVA 203 polyvinyl alcohol solution and 2.2 parts of Ciba® Tinopal® ABP-Z fluorescent whitening agent are mixed with stirring.

The coating composition thus obtained is applied to a base paper [having a pre-coating comprising Ansilex® 93 day (Engelhard Corporation)] weighing 50 g/m² in an amount of about
4 g/m² (on a dry basis), followed by drying and calendering to 400 Bekk seconds smoothness to give a heat sensitive recording paper.

Example 63

A coating composition is prepared as in Example 62 with the exception that in the preparation of Dispersion B-6, 20 parts of 1,2-di(3-methylphenoxy)ethane are replaced with 20 parts p-benzylbiphenyl.

Example 64

A coating composition is prepared as in Example 62 with the exception that in the preparation of Dispersion B-6, 20 parts of 1,2-di(3-methylphenoxy)ethane are replaced with 20 parts 2-benzyl naphthyl ether.

Examples 65-68

Preparation of Dispersion B-7

| | |
|---|---|
| colour developer of Example K | 20 parts |
| 10% aqueous solution of polyvinyl alcohol (PVA 203 manufactured by Kuraray Co. Ltd.) | 13.3 parts |
| 45% aqueous solution of sodium naphthalene sulphonate polymer with formaldehyde | 1.2 parts |
| water | 45.5 parts |

The mixture of the above components is pulverised in a bead mill to a mean particle size of 1.0 μm.

Preparation of Dispersion C-4

| | |
|---|---|
| Diphenyl sulphone | 20 parts |
| 10% aqueous solution of polyvinyl alcohol (PVA-203 manufactured by Kuraray Co. Ltd) | 6.7 parts |
| 45% aqueous solution of sodium naphthalene sulphonate polymer with formaldehyde | 0.8 parts |
| Water | 52.5 parts |

The mixture of the above components is pulverised in a bead mill to a mean particle size of 1.0 μm.

Example 65

40 parts of Dispersion A-3, 80 parts of Dispersion B-7, 80 parts of Dispersion C-4, 50 parts of Dispersion D-7, 38.25 parts of a 17% zinc stearate dispersion (Hidorin F 115, Chukyo Europe), 45 parts of 20% aqueous PVA 203 polyvinyl alcohol solution and 2.2 parts of Ciba® Tinopal® ABP-Z fluorescent whitening agent are mixed with stirring.

The coating composition thus obtained is applied to a base paper [having a pre-coating comprising Ansilex® 93 clay (Engelhard Corporation)] weighing 50 g/m² in an amount of about
4.5 g/m² (on a dry basis), followed by drying and calendering to 400 Bekk seconds smoothness to give a heat sensitive recording paper.

Example 66

A coating composition is prepared as in Example 65 with the exception that in the preparation of Dispersion C4, 20 parts of diphenyl sulphone are replaced with 20 parts dibenzyl terephthalate.

Example 67

A coating composition is prepared as in Example 65 with the exception that in the preparation of Dispersion C-4, 20 parts of diphenyl sulphone are replaced with 20 parts phenyl-1-hydroxy-2-naphthoate.

Example 68

A coating composition is prepared as in Example 65 with the exception that 80 parts of Dispersion C-4 are replaced with 100 parts of a 20% aqueous dispersion of methylol-stearamide (Selosol D-130 manufactured by Chukyo Europe).

Preparation of Dispersion B-8

| | |
|---|---|
| colour developer of Example O | 20 parts |
| 10% aqueous solution of polyvinyl alcohol (PVA 203 manufactured by Kuraray Co. Ltd.) | 13.3 parts |
| 45% aqueous solution of sodium naphthalene sulphonate polymer with formaldehyde | 1.2 parts |
| water | 45.5 parts |

The mixture of the above components is pulverised in a bead mill to a mean particle size of 1.0 μm.

Example 69

40 parts of Dispersion A-3, 80 parts of Dispersion B-8, 80 parts of Dispersion C-3, 50 parts of Dispersion D-7, 38.25 parts of a 17% zinc stearate dispersion (Hidorin F 115, Chukyo Europe), 45 parts of 20% aqueous PVA 203 polyvinyl alcohol solution and 2.2 parts of Ciba® Tinopal® ABP-Z fluorescent whitening agent are mixed with stirring.

The coating composition thus obtained is applied to a base paper [having a pre-mating comprising Ansilex® 93 day (Engelhard Corporation)] weighing 50 g/m² in an amount of about
4.5 g/m² (on a dry basis), followed by drying and calendering to 400 Bekk seconds smoothness to give a heat sensitive recording paper.

Examples 70-72

Example 70

40 parts of Dispersion A-3, 80 parts of Dispersion B-7, 80 parts of Dispersion C-3, 48.3 parts of Dispersion D-7, 20 parts of a 20% aqueous dispersion of stearamide (Hymicron G-270, Chukyo Europe), 20.6 parts of a 17% zinc stearate dispersion (Hidorin F 115, Chukyo Europe), 45 parts of 20% aqueous PVA 203 polyvinyl alcohol solution and 2.2 parts of Ciba® Tinopal® ABP-Z fluorescent whitening agent are mixed with stirring.

The coating composition thus obtained is applied to a base paper [having a pre-coating comprising Ansilex® 93 clay (Engelhard Corporation)] weighing 50 g/m² in an amount of about
4.5 g/m² (on a dry basis), followed by drying and calendering to 400 Bekk seconds smoothness to give a heat sensitive recording paper.

Example 71

A coating composition is prepared as in Example 70 with the exception that in the preparation of Dispersion C-3, 20 parts of 1,2-di(3-methylphenoxy)ethane are replaced with 20 parts 2-benzyl naphthyl ether.

Example 72

A coating composition is prepared as in Example 70 with the exception that in the preparation of Dispersion C-3, 20 parts of 1,2-di(3-methylphenoxy)ethane are replaced with 20 parts p-benzylbiphenyl.

Evaluation of Heat Sensitive Recording Materials

The heat sensitive recording materials prepared according to the invention are evaluated as described below and the results of the evaluations are summarised in Table 1.

Image Optical Density

Using a Thermal Tester (Atlantek Model 200 manufactured by Atlantek Inc.), each heat sensitive recording material is printed at an applied energy of 0.50 mJ/dot and the density of the recorded image thus obtained is measured with a Macbeth 1200 Series densitometer.

Background

The optical density of the unrecorded portion of the heat sensitive material is measured with a Macbeth 1200 Series densitometer.

Heat Resistance

After printing, the heat sensitive recording material is stored for 24 hours in an oven maintained at 60° C. The optical densities of the recorded and unrecorded portions are then measured with a Macbeth densitometer.

Heat/Humidity Resistance

After printing, the heat sensitive recording material is stored for 24 hours in an oven maintained at 40° C. and 90% relative humidity. The optical densities of the recorded and unrecorded portions are then measured with a Macbeth densitometer.

Light Resistance

After printing, the heat sensitive recording material is stored for 18 hours in a xenon weatherometer (Atlas Suntester CPS+, 250 W/m²). The optical densities of the recorded and unrecorded portions are then measured with a Macbeth densitometer.

Oil Resistance

After printing, the heat sensitive recording material is gravure printed with cottonseed oil and then stored for 24 hours in an oven maintained at 40° C. The optical density of the recorded portion is then measured with a Macbeth densitometer.

Plasticiser Resistance

After printing, the heat sensitive recording material is contacted with a PVC strip under 100 g/m² pressure and then stored for 6 hours in an oven maintained at 50° C. The optical density of the recorded portion is then measured with a Macbeth densitometer.

TABLE 1

Evaluation of Heat Sensitive Recording Materials

| Ex. | Optical density (recorded portion) | Optical density (unrecorded portion) | Heat resistance (recorded portion) | Heat resistance (unrecorded portion) | Heat/humidity resistance (recorded portion) |
|---|---|---|---|---|---|
| 1 | 1.20 | 0.05 | 1.22 | 0.17 | 1.20 |
| 2 | 1.30 | 0.06 | 1.30 | 0.18 | 1.36 |
| 3 | 1.17 | 0.05 | 1.22 | 0.09 | 1.22 |
| 4 | 1.28 | 0.05 | 1.31 | 0.09 | 1.38 |

TABLE 1-continued

Evaluation of Heat Sensitive Recording Materials

| | | | | | |
|---|---|---|---|---|---|
| 5 | 1.21 | 0.08 | 1.25 | 0.26 | 1.19 |
| 6 | 1.21 | 0.08 | 1.28 | 0.15 | 1.23 |
| 7 | 1.25 | 0.12 | 1.27 | 0.30 | 1.24 |
| 8 | 1.22 | 0.08 | 1.29 | 0.18 | 1.29 |
| 9 | 1.25 | 0.05 | 1.17 | 0.07 | 1.23 |
| 10 | 1.17 | 0.06 | 1.11 | 0.06 | 1.17 |
| 11 | 1.34 | 0.05 | 1.25 | 0.07 | 1.28 |
| 12 | 1.37 | 0.05 | 1.30 | 0.08 | 1.35 |
| 13 | 1.40 | 0.06 | 1.34 | 0.11 | 1.34 |
| 14 | 1.25 | 0.06 | 1.19 | 0.11 | 1.25 |
| 15 | 1.34 | 0.06 | 1.26 | 0.11 | 1.31 |
| Comp 16 | 1.17 | 0.02 | 1.03 | 0.02 | 1.09 |
| 17 | 1.30 | 0.02 | 1.29 | 0.08 | 1.30 |
| 18 | 1.29 | 0.03 | 1.22 | 0.06 | 1.31 |
| 19 | 1.26 | 0.03 | 1.19 | 0.07 | 1.27 |
| 20 | 1.34 | 0.03 | 1.28 | 0.05 | 1.32 |
| 21 | 1.32 | 0.03 | 1.25 | 0.07 | 1.33 |
| 22 | 1.31 | 0.03 | 1.28 | 0.04 | 1.36 |
| 23 | 1.36 | 0.03 | 1.31 | 0.06 | 1.38 |
| 24 | 1.37 | 0.03 | 1.33 | 0.06 | 1.41 |
| 25 | 1.32 | 0.03 | 1.30 | 0.12 | 1.32 |
| 26 | 1.49 | 0.03 | 1.42 | 0.08 | 1.39 |
| 27 | 1.11 | 0.03 | 0.99 | 0.04 | 0.97 |
| 28 | 1.45 | 0.03 | 1.33 | 0.05 | 1.35 |
| 29 | 1.37 | 0.02 | 1.30 | 0.09 | 1.33 |
| 30 | 1.40 | 0.03 | 1.42 | 0.13 | 1.40 |
| 31 | 1.38 | 0.03 | 1.42 | 0.16 | 1.29 |
| 32 | 1.43 | 0.05 | 1.44 | 0.22 | 1.41 |
| 33 | 1.40 | 0.05 | 1.43 | 0.23 | 1.31 |
| 34 | 1.39 | 0.05 | 1.40 | 0.16 | 1.38 |
| 35 | 1.39 | 0.04 | 1.41 | 0.18 | 1.34 |
| 36 | 1.43 | 0.04 | 1.45 | 0.23 | 1.46 |
| 37 | 1.45 | 0.04 | 1.43 | 0.20 | 1.46 |
| 38 | 1.22 | 0.04 | 1.15 | 0.08 | 1.23 |
| 39 | 1.26 | 0.03 | 1.22 | 0.06 | 1.31 |
| 40 | 1.17 | 0.05 | 1.15 | 0.09 | 1.23 |
| 41 | 1.21 | 0.04 | 1.24 | 0.06 | 1.25 |
| 42 | 1.27 | 0.05 | 1.27 | 0.07 | 1.33 |
| 43 | 1.24 | 0.04 | 1.22 | 0.11 | 1.27 |
| 44 | 1.24 | 0.04 | 1.21 | 0.10 | 1.31 |
| 45 | 1.27 | 0.02 | 1.18 | 0.06 | 1.32 |
| 46 | 1.25 | 0.02 | 1.15 | 0.07 | 1.28 |
| 47 | 1.37 | 0.02 | 1.35 | 0.12 | 1.37 |
| 48 | 1.34 | 0.02 | 1.28 | 0.14 | 1.28 |
| 49 | 1.35 | 0.02 | 1.35 | 0.14 | 1.34 |
| 50 | 1.32 | 0.02 | 1.26 | 0.10 | 1.30 |
| 51 | 1.30 | 0.02 | 1.28 | 0.13 | 1.27 |
| 52 | 1.30 | 0.02 | 1.26 | 0.11 | 1.29 |
| 53 | 1.33 | 0.02 | 1.31 | 0.16 | 1.32 |
| 54 | 1.28 | 0.03 | 1.31 | 0.23 | 1.24 |
| 55 | 1.32 | 0.02 | 1.32 | 0.20 | 1.32 |
| 56 | 1.34 | 0.05 | 1.31 | 0.17 | 1.35 |
| 57 | 1.33 | 0.03 | 1.33 | 0.22 | 1.33 |
| 58 | 1.35 | 0.04 | 1.35 | 0.20 | 1.36 |
| 59 | 1.35 | 0.02 | 1.31 | 0.08 | 1.33 |
| 60 | 1.33 | 0.02 | 1.26 | 0.12 | 1.29 |
| 61 | 1.33 | 0.02 | 1.31 | 0.10 | 1.33 |
| 62 | 1.13 | 0.01 | 1.07 | 0.04 | 1.09 |
| 63 | 1.14 | 0.01 | 1.00 | 0.05 | 0.98 |
| 64 | 1.15 | 0.01 | 1.06 | 0.04 | 1.06 |
| 65 | 1.38 | 0.04 | 1.36 | 0.07 | 1.32 |
| 66 | 1.34 | 0.04 | 1.09 | 0.07 | 1.28 |
| 67 | 1.33 | 0.04 | 1.34 | 0.07 | 1.28 |
| 68 | 1.39 | 0.04 | 1.37 | 0.07 | 1.32 |
| 69 | 1.31 | 0.03 | 1.26 | 0.10 | 1.29 |
| 70 | 1.30 | 0.03 | 1.18 | 0.10 | 1.30 |
| 71 | 1.29 | 0.03 | 1.12 | 0.10 | 1.29 |
| 72 | 1.28 | 0.03 | 1.08 | 0.11 | 1.28 |

| Ex. | Heat/humidity resistance (unrecorded portion) | Light resistance (recorded portion) | Light resistance (unrecorded portion) | Oil resistance (recorded portion) | Plasticiser resistance (recorded portion) |
|---|---|---|---|---|---|
| 1 | 0.15 | 1.06 | 0.10 | 1.15 | 1.21 |
| 2 | 0.16 | 1.18 | 0.11 | 1.21 | 1.25 |
| 3 | 0.07 | 1.08 | 0.10 | 1.15 | 1.21 |
| 4 | 0.06 | 1.17 | 0.11 | 1.22 | 1.26 |

TABLE 1-continued

Evaluation of Heat Sensitive Recording Materials

| | | | | | |
|---|---|---|---|---|---|
| 5 | 0.22 | 1.05 | 0.13 | 1.15 | 1.24 |
| 6 | 0.11 | 1.09 | 0.14 | 1.18 | 1.22 |
| 7 | 0.33 | 1.16 | 0.18 | 1.21 | 1.25 |
| 8 | 0.15 | 1.13 | 0.18 | 1.20 | 1.21 |
| 9 | 0.06 | 1.17 | 0.07 | 1.10 | 1.21 |
| 10 | 0.08 | 1.05 | 0.08 | 0.36 | 0.95 |
| 11 | 0.05 | 1.22 | 0.08 | 1.26 | 1.26 |
| 12 | 0.05 | 1.28 | 0.07 | 1.27 | 1.29 |
| 13 | 0.06 | 1.27 | 0.07 | 1.16 | 1.31 |
| 14 | 0.07 | 1.18 | 0.08 | 1.26 | 1.19 |
| 15 | 0.07 | 1.26 | 0.08 | 1.27 | 1.27 |
| Comp 16 | 0.03 | 1.02 | 0.03 | 0.33 | 0.72 |
| 17 | 0.05 | 1.21 | 0.06 | 1.25 | 1.27 |
| 18 | 0.06 | 1.22 | 0.03 | 1.30 | 1.29 |
| 19 | 0.05 | 1.18 | 0.05 | 1.26 | 1.26 |
| 20 | 0.06 | 1.24 | 0.04 | 1.33 | 1.33 |
| 21 | 0.05 | 1.22 | 0.06 | 1.29 | 1.31 |
| 22 | 0.05 | 1.21 | 0.03 | 1.31 | 1.27 |
| 23 | 0.07 | 1.30 | 0.03 | 1.39 | 1.35 |
| 24 | 0.08 | 1.34 | 0.04 | 1.37 | 1.36 |
| 25 | 0.11 | 1.26 | 0.05 | 1.34 | 1.33 |
| 26 | 0.07 | 0.25 | 0.19 | 1.40 | 1.27 |
| 27 | 0.02 | 0.37 | 0.12 | 0.77 | 0.56 |
| 28 | 0.04 | 0.96 | 0.15 | 0.77 | 0.78 |
| 29 | 0.06 | 0.65 | 0.18 | 1.30 | 1.18 |
| 30 | 0.06 | 1.35 | 0.07 | 1.37 | 1.40 |
| 31 | 0.08 | 1.31 | 0.07 | 1.33 | 1.36 |
| 32 | 0.18 | 1.39 | 0.31 | 1.39 | 1.42 |
| 33 | 0.19 | 1.34 | 0.30 | 1.34 | 1.42 |
| 34 | 0.15 | 1.35 | 0.10 | 1.42 | 1.30 |
| 35 | 0.17 | 1.22 | 0.12 | 1.33 | 1.39 |
| 36 | 0.20 | 1.03 | 0.18 | 1.43 | 1.41 |
| 37 | 0.17 | 1.37 | 0.12 | 1.41 | 1.42 |
| 38 | 0.06 | 1.02 | 0.06 | 1.11 | 1.03 |
| 39 | 0.05 | 1.14 | 0.07 | 1.12 | 1.21 |
| 40 | 0.08 | 1.06 | 0.08 | 1.11 | 1.17 |
| 41 | 0.06 | 1.13 | 0.09 | 1.15 | 1.24 |
| 42 | 0.08 | 1.19 | 0.07 | 1.23 | 1.26 |
| 43 | 0.07 | 1.14 | 0.09 | 1.09 | 1.21 |
| 44 | 0.10 | 1.06 | 0.07 | 1.11 | 1.22 |
| 45 | 0.06 | 1.19 | 0.06 | 1.10 | 1.18 |
| 46 | 0.04 | 1.11 | 0.04 | 1.10 | 1.15 |
| 47 | 0.08 | 1.31 | 0.03 | 1.37 | 1.36 |
| 48 | 0.09 | 1.23 | 0.03 | 1.18 | 1.32 |
| 49 | 0.11 | 1.24 | 0.03 | 1.24 | 1.33 |
| 50 | 0.07 | 1.22 | 0.06 | 1.25 | 1.25 |
| 51 | 0.07 | 1.19 | 0.07 | 1.14 | 1.26 |
| 52 | 0.07 | 1.14 | 0.06 | 1.17 | 1.26 |
| 53 | 0.19 | 1.32 | 0.06 | 1.35 | 1.33 |
| 54 | 0.20 | 1.16 | 0.07 | 1.25 | 1.28 |
| 55 | 0.19 | 1.22 | 0.06 | 1.29 | 1.33 |
| 56 | 0.25 | 1.28 | 0.08 | 1.35 | 1.32 |
| 57 | 0.23 | 1.22 | 0.06 | 1.28 | 1.34 |
| 58 | 0.24 | 1.21 | 0.08 | 1.31 | 1.37 |
| 59 | 0.07 | 1.23 | 0.04 | 1.28 | 1.26 |
| 60 | 0.07 | 1.19 | 0.04 | 1.23 | 1.25 |
| 61 | 0.07 | 1.19 | 0.04 | 1.25 | 1.26 |
| 62 | 0.02 | 0.96 | 0.05 | 0.90 | 1.05 |
| 63 | 0.03 | 0.93 | 0.05 | 0.84 | 1.04 |
| 64 | 0.03 | 0.94 | 0.06 | 0.84 | 1.05 |
| 65 | 0.08 | 1.28 | 0.07 | 1.30 | 1.33 |
| 66 | 0.08 | 1.11 | 0.06 | 1.27 | 1.20 |
| 67 | 0.08 | 1.22 | 0.12 | 1.28 | 1.29 |
| 68 | 0.08 | 1.32 | 0.06 | 1.35 | 1.30 |
| 69 | 0.06 | 1.21 | 0.06 | 1.27 | 1.19 |
| 70 | 0.06 | 1.17 | 0.06 | 1.26 | 1.30 |
| 71 | 0.06 | 1.10 | 0.06 | 1.16 | 1.29 |
| 72 | 0.06 | 1.05 | 0.06 | 1.18 | 1.28 |

The invention claimed is:
1. A mixture consisting of
(a) a color developer (1a)

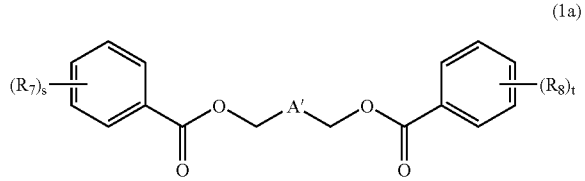

wherein
A' stands for a unsubstituted or substituted divalent aromatic radical,
$R_7$ and $R_8$ are independent of each other and stand for —OH, unsubstituted or substituted $C_1$-$C_8$alkyl, unsubstituted or substituted $C_1$-$C_8$alkoxy, unsubstituted or substituted phenyl or naphthyl, —$COOR_{1a}$, wherein $R_{1a}$ stands for hydrogen, unsubstituted or substituted $C_1$-$C_8$alkyl, benzyl or unsubstituted or substituted phenyl, —$C(O)R_{1a}$, or —$NR_{1a}R_{1b}$, wherein $R_{1b}$, independently from $R_{1a}$, stands for hydrogen, unsubstituted or substituted $C_1$-$C_8$alkyl, benzyl or unsubstituted or substituted phenyl, s stands for 0, 1, 2, 3, 4 or 5, t stands for 0, 1, 2, 3, 4, or 5, and
(b) a compound of formula (2)

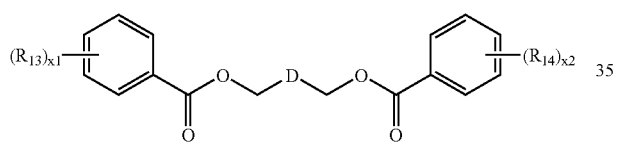

wherein D stands for

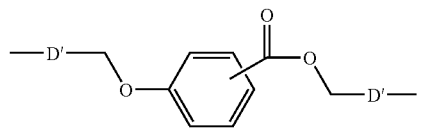

wherein D' stands for a unsubstituted or substituted divalent aromatic radical, $R_{13}$ stands for a substituent as defined for $R_7$, $R_{14}$ stands for a substituent as defined for $R_8$, x1 stands for 0, 1, 2, 3, 4 or 5, x2 stands for 0, 1, 2, 3, 4, or 5,
and wherein the weight ratio of (1a) to (2) is chosen in the range from 99.9:0.1 to 0.1:99.9.

2. A heat sensitive composition consisting of
a) a colour forming compound, and
b) a mixture of colour developer of the formula (1a) and compound of formula (2) as defined in claim 1.

3. A process for the manufacture of a heat sensitive recording material by incorporating the mixture of developer (1a) and compound (2) as defined in claim 1 into a coating composition which is applied to a substrate to generate a heat sensitive recording material.

4. A process for the manufacture of a heat sensitive recording material by incorporating the compound of formula (2) as defined in claim 1 into a coating composition which is applied to a substrate to generate the heat sensitive recording material.

5. A process for the manufacture of a mixture of colour developer (1)

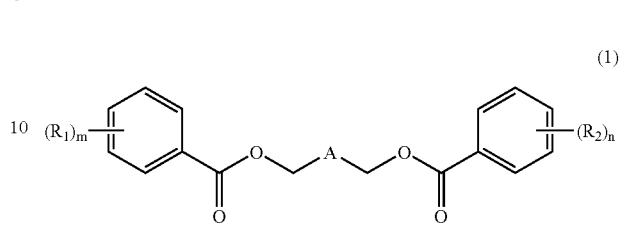

wherein
A stands for a unsubstituted or substituted divalent aromatic radical, and
$R_1$ and $R_2$ are independent of each other and stand for —OH, unsubstituted or substituted $C_1$-$C_8$alkyl, unsubstituted or substituted $C_1$-$C_8$alkoxy, unsubstituted or substituted phenyl or naphthyl, —$COOR_{1a}$, wherein $R_{1a}$ stands for hydrogen, unsubstituted or substituted $C_1$-$C_8$alkyl, benzyl or unsubstituted or substituted phenyl, —$C(O)R_{1a}$, or —$NR_{1a}R_{1b}$, wherein $R_{1b}$, independently from $R_{1a}$, stands for hydrogen, unsubstituted or substituted $C_1$-$C_8$alkyl, benzyl or unsubstituted or substituted phenyl, m stands for 0, 1, 2, 3, 4 or 5, n stands for 0, 1, 2, 3, 4, or 5, with the proviso, that if A stands for para-phenylene, $R_1$ for hydroxy (m≠0), then $R_2$ is not hydroxyl,
and compound of formula (2)

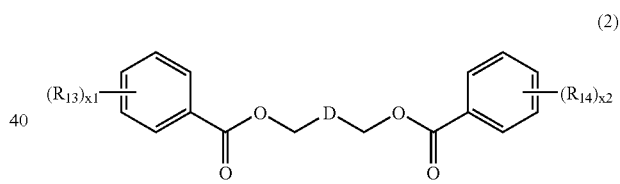

wherein D stands for

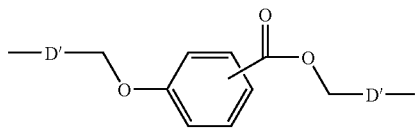

wherein D' stands for a unsubstituted or substituted divalent aromatic radical, $R_{13}$ stands for a substituent as defined for $R_7$, $R_{14}$ stands for a substituent as defined for $R_8$, x1 stands for 0, 1, 2, 3, 4 or 5, x2 stands for 0, 1, 2, 3, 4, or 5,
$R_7$ and $R_8$ are independent of each other and stand for —OH, unsubstituted or substituted $C_1$-$C_8$alkyl, unsubstituted or substituted $C_1$-$C_8$alkoxy, unsubstituted or substituted phenyl or naphthyl, —$COOR_{1a}$, wherein $R_{1a}$ is defined as above, —$C(O)R_{1a}$, or —$NR_{1a}R_{1b}$, wherein $R_{1b}$ is defined as above,
by reacting a benzoic acid derivative with a dihalogen derivative, characterized in (a) reacting benzoic acid derivative of formula (A1)

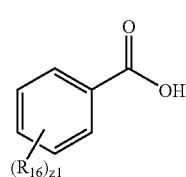

with a dihalogen derivative of formula (B1)

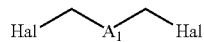

wherein $R_{16}$ stands for —OH, unsubstituted or substituted $C_1$-$C_8$alkyl, unsubstituted or substituted $C_1$-$C_8$alkoxy, unsubstituted or substituted phenyl or naphthyl, —COOR$_{1a}$, wherein R$_{1a}$ stands for hydrogen, unsubstituted or substituted $C_1$-$C_8$alkyl, benzyl or unsubstituted or substituted phenyl, —C(O)R$_{1a}$, or —NR$_{1a}$R$_{1b}$, wherein R$_{1b}$, independently from R$_{1a}$, stands for hydrogen, unsubstituted or substituted $C_1$-$C_8$alkyl, benzyl or unsubstituted or substituted phenyl, z1 stands for 0, 1, 2, 3, 4 or 5, A$_1$ stands for a unsubstituted or substituted divalent aromatic radical, or (b) reacting a mixture of benzoic derivatives (A1) and (A2)

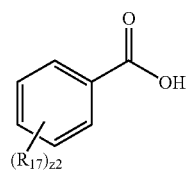

with a dihalogen derivative of formula (B1),
wherein $R_{17}$, different from $R_{16}$, stands for —OH, unsubstituted or substituted $C_1$-$C_8$alkyl, unsubstituted or substituted $C_1$-$C_8$alkoxy, unsubstituted or substituted phenyl or naphthyl, —COOR$_{1a}$, —C(O)R$_{1a}$, or —NR$_{1a}$R$_{1b}$, z2 stands for 0, 1, 2, 3, 4 or 5, or (c) reacting benzoic acid derivative of formula (A1) with dihalogen derivative (B1) to yield compound (C1)

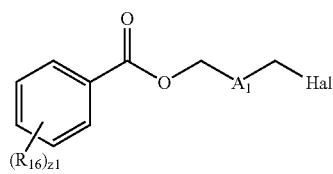

and then reacting compound (C1) with compound of formula (A2),
wherein the molar ratio of (A1) or ((A1)+(A2)) to (B1) is chosen in the range of less than 3:1.

6. A mixture of a color developer of formula (1)

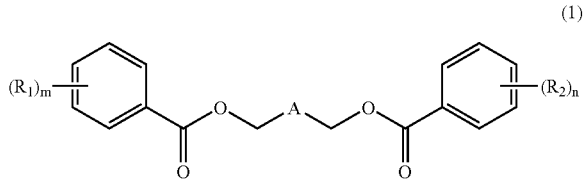

wherein
A stands for a unsubstituted or substituted divalent aromatic radical, and
$R_1$ and $R_2$ are independent of each other and stand for —OH, unsubstituted or substituted $C_1$-$C_8$alkyl, unsubstituted or substituted $C_1$-$C_8$alkoxy, unsubstituted or substituted phenyl or naphthyl, —COOR$_{1a}$, wherein R$_{1a}$ stands for hydrogen, unsubstituted or substituted $C_1$-$C_8$alkyl, benzyl or unsubstituted or substituted phenyl, —C(O)R$_{1a}$, or —NR$_{1a}$R$_{1b}$, wherein R$_{1b}$, independently from R$_{1a}$, stands for hydrogen, unsubstituted or substituted $C_1$-$C_8$alkyl, benzyl or unsubstituted or substituted phenyl, m stands for 0, 1, 2, 3, 4 or 5, n stands for 0, 1, 2, 3, 4, or 5, with the proviso, that if A stands for para-phenylene, $R_1$ for hydroxy (m≠0), then $R_2$ is not hydroxyl, and a compound of formula (2)

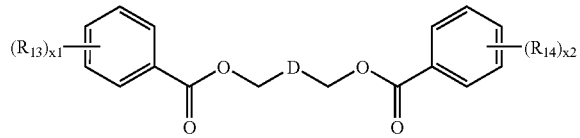

wherein D stands for

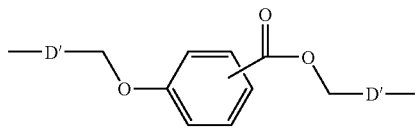

wherein D' stands for a unsubstituted or substituted divalent aromatic radical, $R_{13}$ stands for a substituent as defined for $R_7$, $R_{14}$ stands for a substituent as defined for $R_8$, x1 stands for 0, 1, 2, 3, 4 or 5, x2 stands for 0, 1, 2, 3, 4, or 5,
$R_7$ and $R_8$ are independent of each other and stand for —OH, unsubstituted or substituted $C_1$-$C_8$alkyl, unsubstituted or substituted $C_1$-$C_8$alkoxy, unsubstituted or substituted phenyl or naphthyl, —COOR$_{1a}$, wherein R$_{1a}$ is defined as above, —C(O)R$_{1a}$, or —NR$_{1a}$R$_{1b}$, wherein R$_{1b}$ is defined as above,
wherein the mixture is a product by the process as defined in claim 5.

7. A process for the manufacture of compound (2)

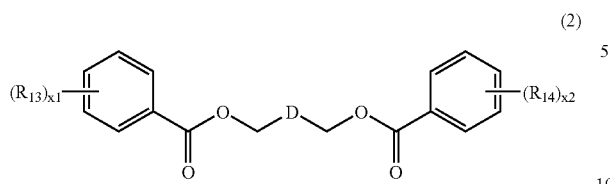

wherein D stands for

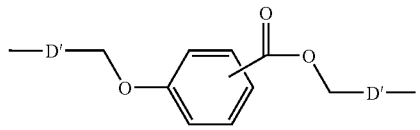

wherein D' stands for a unsubstituted or substituted divalent aromatic radical, $R_{13}$ stands for a substituent as defined for $R_7$, $R_{14}$ stands for a substituent as defined for $R_8$, x1 stands for 0, 1, 2, 3, 4 or 5, x2 stands for 0, 1, 2, 3, 4, or 5, $R_7$ and $R_8$ are independent of each other and stand for —OH, unsubstituted or substituted $C_1$-$C_8$alkyl, unsubstituted or substituted $C_1$-$C_8$alkoxy, unsubstituted or substituted phenyl or naphthyl, —COOR$_{1a}$, wherein R$_{1a}$ is stands for hydrogen, unsubstituted or substituted $C_1$-$C_8$alkyl, benzyl or unsubstituted or substituted phenyl, —C(O)R$_{1a}$, or —NR$_{1a}$R$_{1b}$, wherein R$_{1b}$ independently from R$_{1a}$, stands for hydrogen, unsubstituted or substituted $C_1$-$C_8$alkyl, benzyl or unsubstituted or substituted phenyl, characterized in reacting compound (C1)

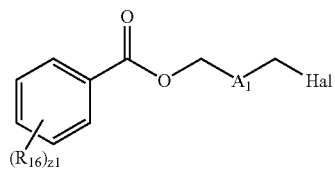

$A_1$ stands for a unsubstituted or substituted divalent aromatic radical, wherein $R_{16}$ stands for —OH, unsubstituted or substituted $C_1$-$C_8$alkyl, unsubstituted or substituted $C_1$-$C_8$alkoxy, unsubstituted or substituted phenyl or naphthyl, —COOR$_{1a}$ and R$_{1a}$ is defined as above, —C(O)R$_{1a}$, or —NR$_{1a}$R$_{1b}$, wherein R$_{1b}$ is defined as above, and z1 stands for 0, 1, 2, 3, 4 or 5, with color developer (1),

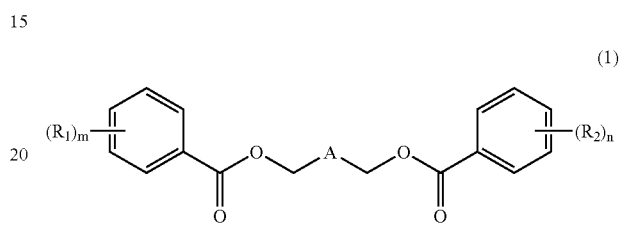

wherein

A stands for a unsubstituted or substituted divalent aromatic radical, and $R_1$ and $R_2$ are independent of each other and stand for —OH, unsubstituted or substituted $C_1$-$C_8$alkyl, unsubstituted or substituted $C_1$-$C_8$alkoxy, unsubstituted or substituted phenyl or naphthyl, —COOR$_{1a}$, wherein R$_{1a}$ stands for hydrogen, unsubstituted or substituted $C_1$-$C_8$alkyl, benzyl or unsubstituted or substituted phenyl, —C(O)R$_{1a}$, or —NR$_{1a}$R$_{1b}$, wherein R$_{1b}$, independently from R$_{1a}$, stands for hydrogen, unsubstituted or substituted $C_1$-$C_8$alkyl, benzyl or unsubstituted or substituted phenyl, n stands for 0, 1, 2, 3, 4, or 5 and where $R_1$ and/or $R_2$ of developer (1) is hydroxy and m is 1, 2, 3, 4 or 5, with the proviso, that if A stands for para-phenylene and $R_1$ for hydroxy, then $R_2$ is not hydroxy.

* * * * *